(12) United States Patent
Yee

(10) Patent No.: US 11,471,582 B2
(45) Date of Patent: Oct. 18, 2022

(54) VACUUM TRANSFER TOOL FOR EXTENDABLE CATHETER

(71) Applicant: INCEPT, LLC, Lexington, MA (US)

(72) Inventor: Brandon Yee, Oakland, CA (US)

(73) Assignee: Incept, LLC, Lexington, MA (US)

( * ) Notice: Subject to any disclaimer, the term of this patent is extended or adjusted under 35 U.S.C. 154(b) by 308 days.

(21) Appl. No.: 16/503,886

(22) Filed: Jul. 5, 2019

(65) Prior Publication Data

US 2020/0009301 A1   Jan. 9, 2020

Related U.S. Application Data

(60) Provisional application No. 62/694,792, filed on Jul. 6, 2018.

(51) Int. Cl.
 A61M 1/00  (2006.01)
 A61M 39/22 (2006.01)
 (Continued)

(52) U.S. Cl.
 CPC .......... *A61M 1/74* (2021.05); *A61M 25/0023* (2013.01); *A61M 39/22* (2013.01); *A61B 2217/005* (2013.01); *A61M 2025/091* (2013.01)

(58) Field of Classification Search
 CPC .... A61M 1/74; A61M 39/22; A61M 25/0023; A61M 2025/091; A61M 1/743;
 (Continued)

(56) References Cited

U.S. PATENT DOCUMENTS 3,605,750 A    9/1971  Sheridan et al.
3,884,242 A    5/1975  Bazell et al.
(Continued)

FOREIGN PATENT DOCUMENTS

CN    110916768    3/2020
DE     8900059     5/1989
(Continued)

OTHER PUBLICATIONS

U.S. Appl. No. 15/443,841 (U.S. Pat. No. 10,661,053), filed Feb. 27, 2017, Method of Pulsatile Neurovascular Aspiration With Telescoping Catheter.
(Continued)

*Primary Examiner* — Amber R Stiles
*Assistant Examiner* — Avery Smale
(74) *Attorney, Agent, or Firm* — Knobbe, Martens, Olson & Bear, LLP

(57) ABSTRACT

An aspiration catheter is provided including a proximal section and a distal section extendable through the proximal section. A vacuum transfer tool may be coupled to a proximal end of the proximal section. The vacuum transfer tool may include a proximal transfer tube and a distal transfer tube, each having an aspiration port in communication with a vacuum source. The proximal transfer tube may be removably received within a proximal end of the distal transfer tube. The proximal transfer tube may maintain a vacuum around the proximal end of the distal section of the catheter such that when the distal section is removed by decoupling the proximal and distal transfer tubes, the vacuum within the distal transfer tube and proximal section of the catheter is maintained, preventing the escape of any clots.

14 Claims, 21 Drawing Sheets

(51) Int. Cl.
*A61M 25/00* (2006.01)
*A61M 25/09* (2006.01)

(58) Field of Classification Search
CPC .. A61M 1/75; A61M 1/84; A61M 2025/0004; A61B 2217/005; A61B 17/22004; A61B 2017/22044; A61B 17/22; A61B 2017/00154; A61B 2017/00991
See application file for complete search history.

(56) References Cited

U.S. PATENT DOCUMENTS

| | | | |
|---|---|---|---|
| 3,890,976 | A | 6/1975 | Bazell et al. |
| 3,965,901 | A | 6/1976 | Penny et al. |
| 4,030,503 | A | 6/1977 | Clark, III |
| 4,319,580 | A | 3/1982 | Colley et al. |
| 4,611,594 | A | 9/1986 | Grayhack et al. |
| 4,617,019 | A | 10/1986 | Fecht et al. |
| 4,619,274 | A | 10/1986 | Morrison et al. |
| 4,628,168 | A | 12/1986 | Nebergall et al. |
| 4,762,129 | A | 8/1988 | Bonzel |
| 4,762,130 | A | 8/1988 | Fogarty et al. |
| 4,767,399 | A | 8/1988 | Bollish |
| 4,810,582 | A | 3/1989 | Gould et al. |
| 4,844,064 | A | 7/1989 | Thimsen et al. |
| 4,898,575 | A | 2/1990 | Fischell et al. |
| 4,923,462 | A | 5/1990 | Stevens |
| 5,011,488 | A | 4/1991 | Ginsburg |
| 5,040,548 | A | 8/1991 | Yock |
| 5,103,827 | A | 4/1992 | Smith |
| 5,120,323 | A | 6/1992 | Shockey et al. |
| 5,217,705 | A | 6/1993 | Reno et al. |
| 5,226,909 | A | 7/1993 | Evans et al. |
| 5,234,416 | A | 8/1993 | Macaulay et al. |
| 5,243,997 | A | 9/1993 | Uflacker |
| 5,261,916 | A | 11/1993 | Engelson et al. |
| 5,290,247 | A | 3/1994 | Crittenden |
| 5,308,327 | A | 5/1994 | Heaven et al. |
| 5,328,472 | A | 7/1994 | Steinke et al. |
| 5,413,560 | A | 5/1995 | Solar |
| 5,417,697 | A | 5/1995 | Wilk |
| 5,423,846 | A | 6/1995 | Fischell |
| 5,439,445 | A | 8/1995 | Kontos |
| 5,441,051 | A | 8/1995 | Hileman et al. |
| 5,454,795 | A | 10/1995 | Samson |
| 5,466,222 | A | 11/1995 | Ressemann et al. |
| 5,474,563 | A | 12/1995 | Myler et al. |
| 5,527,292 | A | 6/1996 | Adams et al. |
| 5,549,119 | A | 8/1996 | Solar |
| 5,569,178 | A | 10/1996 | Henley |
| 5,569,277 | A | 10/1996 | Evans et al. |
| 5,591,187 | A | 1/1997 | Dekel |
| 5,643,254 | A | 7/1997 | Scheldrup et al. |
| 5,658,263 | A | 8/1997 | Dang et al. |
| 5,662,622 | A | 9/1997 | Gore et al. |
| 5,690,613 | A | 11/1997 | Verbeek |
| 5,695,483 | A | 12/1997 | Samson |
| 5,702,373 | A | 12/1997 | Samson |
| 5,766,191 | A | 6/1998 | Trerotola |
| 5,776,141 | A | 7/1998 | Klein et al. |
| 5,827,242 | A | 10/1998 | Follmer |
| 5,843,103 | A | 12/1998 | Wulfman |
| 5,873,882 | A | 2/1999 | Straub et al. |
| 5,876,414 | A | 3/1999 | Straub |
| 5,885,209 | A | 3/1999 | Green |
| 5,891,114 | A | 4/1999 | Chien et al. |
| 5,895,398 | A | 4/1999 | Wensel |
| 5,899,892 | A | 5/1999 | Mortier et al. |
| 5,916,192 | A | 6/1999 | Nita et al. |
| 5,935,112 | A * | 8/1999 | Stevens .............. A61M 39/0613 604/246 |
| 5,951,539 | A | 9/1999 | Nita |
| 6,007,530 | A | 12/1999 | Dornhofer et al. |
| 6,056,837 | A | 5/2000 | Lieber et al. |
| 6,059,745 | A | 5/2000 | Gelbfish |
| 6,090,118 | A | 7/2000 | McGuckin, Jr. |
| 6,159,230 | A | 12/2000 | Samuels |
| 6,165,163 | A | 12/2000 | Chien et al. |
| 6,165,199 | A | 12/2000 | Barbut |
| 6,171,295 | B1 | 1/2001 | Garabedian et al. |
| 6,179,859 | B1 | 1/2001 | Bates |
| 6,197,014 | B1 | 3/2001 | Samson et al. |
| 6,206,852 | B1 | 3/2001 | Lee |
| 6,217,557 | B1 | 4/2001 | Hakansson et al. |
| 6,221,038 | B1 | 4/2001 | Brisken |
| 6,228,046 | B1 | 5/2001 | Brisken |
| 6,258,052 | B1 | 7/2001 | Milo |
| 6,267,783 | B1 | 7/2001 | Letendre et al. |
| 6,285,903 | B1 | 9/2001 | Rosenthal |
| 6,355,027 | B1 | 3/2002 | Le et al. |
| 6,394,976 | B1 | 5/2002 | Winston et al. |
| 6,451,036 | B1 | 6/2002 | Heitzmann |
| 6,451,005 | B1 | 9/2002 | Saitou et al. |
| 6,458,139 | B1 | 10/2002 | Palmer et al. |
| 6,468,219 | B1 | 10/2002 | Njemanze |
| 6,482,217 | B1 | 11/2002 | Pintor et al. |
| 6,511,492 | B1 | 1/2003 | Rosenbluth |
| 6,524,303 | B1 | 2/2003 | Garibaldi et al. |
| 6,520,934 | B1 | 3/2003 | Lee |
| 6,533,751 | B2 | 3/2003 | Cragg |
| 6,554,820 | B1 | 4/2003 | Wendlandt |
| 6,554,827 | B2 | 4/2003 | Chandrasekaran et al. |
| 6,558,377 | B2 | 5/2003 | Lee et al. |
| 6,569,148 | B2 | 5/2003 | Bagaoisan et al. |
| 6,579,246 | B2 | 6/2003 | Jacobsen et al. |
| 6,582,440 | B1 | 6/2003 | Brumbach |
| 6,591,472 | B1 | 7/2003 | Noone et al. |
| 6,638,268 | B2 | 10/2003 | Niazi |
| 6,666,874 | B2 | 12/2003 | Heitzmann |
| 6,669,670 | B1 | 12/2003 | Muni et al. |
| 6,719,717 | B1 | 4/2004 | Johnson et al. |
| 6,776,770 | B1 | 8/2004 | Trerotola |
| 6,824,550 | B1 | 11/2004 | Pintor et al. |
| 6,977,068 | B1 | 12/2005 | Nair et al. |
| 7,004,954 | B1 | 2/2006 | Voss et al. |
| 7,008,434 | B2 | 3/2006 | Kurz et al. |
| 7,029,482 | B1 | 4/2006 | Vargas |
| 7,037,267 | B1 | 5/2006 | Lipson et al. |
| 7,104,979 | B2 | 9/2006 | Jansen et al. |
| 7,112,298 | B2 | 9/2006 | Kampa et al. |
| 7,172,620 | B2 | 2/2007 | Gilson |
| 7,175,653 | B2 | 2/2007 | Gaber |
| 7,207,980 | B2 | 4/2007 | Christian et al. |
| 7,223,274 | B2 | 5/2007 | Vargas |
| 7,229,461 | B2 | 6/2007 | Chin et al. |
| 7,232,452 | B2 | 6/2007 | Adams et al. |
| 7,235,088 | B2 | 6/2007 | Pintor et al. |
| 7,306,585 | B2 | 12/2007 | Ross |
| 7,309,334 | B2 | 12/2007 | von Hoffmann |
| 7,335,216 | B2 | 2/2008 | Bender |
| 7,491,210 | B2 | 2/2009 | Dubrul et al. |
| 7,507,229 | B2 | 3/2009 | Hewitt et al. |
| 7,537,568 | B2 | 5/2009 | Moehring |
| 7,558,622 | B2 | 7/2009 | Tran |
| 7,601,138 | B2 | 10/2009 | Goebel et al. |
| 7,678,100 | B2 | 3/2010 | Chin et al. |
| 7,713,227 | B2 | 5/2010 | Wholey et al. |
| 7,763,196 | B2 | 7/2010 | Goebel et al. |
| 7,771,358 | B2 | 8/2010 | Moehring et al. |
| 7,803,136 | B2 | 9/2010 | Schatz |
| 7,837,692 | B2 | 11/2010 | Mulholland et al. |
| 7,842,055 | B2 | 11/2010 | Pintor et al. |
| 7,850,623 | B2 | 12/2010 | Griffin |
| 7,905,891 | B2 | 3/2011 | Self |
| 7,931,659 | B2 | 4/2011 | Bose et al. |
| 7,938,820 | B2 | 5/2011 | Webster et al. |
| 7,988,646 | B2 | 8/2011 | Taber |
| 8,021,351 | B2 | 9/2011 | Boldenow et al. |
| 8,048,032 | B2 | 11/2011 | Root et al. |
| 8,057,497 | B1 | 11/2011 | Raju et al. |
| 8,062,316 | B2 | 11/2011 | Patel |
| 8,070,694 | B2 | 12/2011 | Galdonik et al. |
| 8,084,246 | B2 | 12/2011 | Hoon et al. |
| 8,114,106 | B2 | 2/2012 | Straub |

(56) References Cited

U.S. PATENT DOCUMENTS

| | | |
|---|---|---|
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,298,591 B2 | 10/2012 | Srivastava et al. |
| 8,361,095 B2 | 1/2013 | Osborne |
| 8,366,735 B2 | 2/2013 | Bose et al. |
| 8,382,739 B2 | 2/2013 | Walak et al. |
| 8,394,078 B2 | 3/2013 | Torrance et al. |
| 8,403,912 B2 | 3/2013 | McFerran et al. |
| 8,460,312 B2 | 6/2013 | Bose et al. |
| 8,485,969 B2 | 7/2013 | Grayzel et al. |
| 8,517,955 B2 | 8/2013 | Keast |
| 8,535,293 B2 | 9/2013 | Faherty et al. |
| 8,568,432 B2 | 10/2013 | Straub |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |
| 8,684,963 B2 | 4/2014 | Qiu et al. |
| 8,696,698 B2 | 4/2014 | Chomas |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse |
| 8,876,854 B2 | 11/2014 | Christiansen et al. |
| 8,900,257 B2 | 12/2014 | Straub et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,996,095 B2 | 3/2015 | Anderson et al. |
| 8,998,946 B2 | 4/2015 | Morero et al. |
| 9,014,786 B2 | 4/2015 | Carmeli et al. |
| 9,017,309 B2 | 4/2015 | Tanikawa et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,199,064 B2 | 12/2015 | Morero |
| 9,238,124 B2 | 1/2016 | Grayzel et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,345,856 B2 | 5/2016 | Witte |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,440,018 B2 | 9/2016 | Levin et al. |
| 9,446,216 B2 | 9/2016 | Olesky et al. |
| 9,451,884 B2 | 9/2016 | Palovich |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,764,111 B2 | 9/2017 | Gulachenski |
| 9,770,251 B2 | 9/2017 | Bowman et al. |
| 9,789,242 B2 | 9/2017 | Criado et al. |
| 9,775,730 B1 | 10/2017 | Waltzman |
| 9,789,283 B2 | 10/2017 | Richter et al. |
| 9,801,643 B2 | 10/2017 | Hansen et al. |
| 9,803,043 B2 | 10/2017 | Cruise et al. |
| 9,808,610 B2 | 11/2017 | Li et al. |
| 9,820,761 B2 | 11/2017 | Garrison et al. |
| 9,827,047 B2 | 11/2017 | Fudaba et al. |
| 9,855,072 B2 | 1/2018 | Moberg et al. |
| 9,861,783 B2 | 1/2018 | Garrison et al. |
| 9,877,731 B2 | 1/2018 | Cruise et al. |
| 9,907,880 B2 | 1/2018 | Cruise et al. |
| 9,883,885 B2 | 2/2018 | Hendrick et al. |
| 9,913,960 B2 | 3/2018 | Blanchard et al. |
| 9,987,028 B2 | 6/2018 | Lowinger et al. |
| 9,999,355 B2 | 6/2018 | Kirenko |
| 10,010,698 B2 | 7/2018 | Watanabe et al. |
| 10,028,854 B2 | 7/2018 | Tatalovich et al. |
| 10,039,906 B2 | 8/2018 | Kume et al. |
| 10,070,878 B2 | 9/2018 | Ma |
| 10,086,169 B2 | 10/2018 | Grayzel et al. |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,207,077 B2 | 2/2019 | Griggin et al. |
| 10,213,582 B2 | 2/2019 | Garrison et al. |
| 10,226,277 B2 | 3/2019 | Smith et al. |
| 10,238,833 B2 | 3/2019 | Christian et al. |
| 10,258,452 B2 | 4/2019 | Eckhouse et al. |
| 10,265,086 B2 | 4/2019 | Vale et al. |
| 10,271,864 B2 | 4/2019 | Greenhalgh et al. |
| 10,278,678 B2 | 5/2019 | Peliks |
| 10,278,816 B2 | 5/2019 | Miller et al. |
| 10,327,790 B2 | 6/2019 | Garrison et al. |
| 10,335,186 B2 | 7/2019 | Rosenbluth et al. |
| 10,342,570 B2 | 7/2019 | Richter et al. |

(56) References Cited

U.S. PATENT DOCUMENTS

| | | |
|---|---|---|
| 10,383,691 B2 | 8/2019 | Hendrick et al. |
| 10,384,034 B2 | 8/2019 | Garrison et al. |
| 10,420,581 B2 | 9/2019 | Hehrlein et al. |
| 10,456,552 B2 | 10/2019 | Goyal |
| 10,471,233 B2 | 11/2019 | Garrison et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,569,049 B2 | 2/2020 | Garrison et al. |
| 10,610,668 B2 | 4/2020 | Burkholz et al. |
| 10,646,239 B2 | 5/2020 | Garrison et al. |
| 10,653,434 B1 | 5/2020 | Yang et al. |
| 10,668,192 B2 | 6/2020 | Raney et al. |
| 10,695,159 B2 | 6/2020 | Hauser |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,786,270 B2 | 9/2020 | Yang |
| 10,856,898 B2 | 12/2020 | Matsushita et al. |
| 10,888,280 B2 | 1/2021 | Newberry |
| 10,905,850 B2 | 2/2021 | Christian et al. |
| 11,020,030 B2 | 6/2021 | Tao et al. |
| 11,065,018 B2 | 7/2021 | Buck et al. |
| 11,076,876 B2 | 8/2021 | Vale |
| 11,197,683 B1 | 12/2021 | Teigen et al. |
| 11,207,096 B2 | 12/2021 | To et al. |
| 11,207,497 B1 | 12/2021 | Yee et al. |
| 11,259,821 B2 | 3/2022 | Buck et al. |
| 2001/0031980 A1 | 10/2001 | Wensel et al. |
| 2001/0031981 A1 | 10/2001 | Evans |
| 2001/0049486 A1 | 12/2001 | Evans et al. |
| 2002/0016565 A1* | 2/2002 | Zadno-Azizi ..... A61M 25/0009 604/101.03 |
| 2002/0026145 A1 | 2/2002 | Bagaoisan et al. |
| 2002/0074276 A1 | 6/2002 | Nakashima |
| 2002/0091372 A1 | 7/2002 | Cragg |
| 2002/0156459 A1 | 10/2002 | Ye et al. |
| 2002/0156460 A1 | 10/2002 | Ye |
| 2002/0169467 A1 | 11/2002 | Heitzmann |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1 | 10/2004 | Kellett |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082375 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |
| 2013/0131710 A1 | 5/2013 | Carmeli |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0271718 A1 | 9/2014 | Alvarez |

(56) References Cited

U.S. PATENT DOCUMENTS

| | | |
|---|---|---|
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisei et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0269825 A1 | 9/2015 | Tran |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1* | 12/2015 | Vale ............... A61B 17/221 606/115 |
| 2015/0366518 A1 | 12/2015 | Sampson |
| 2016/0000443 A1 | 1/2016 | Lilburn et al. |
| 2016/0008572 A1 | 1/2016 | Di Caprio |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0071624 A1 | 3/2017 | McGuckin et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0238950 A1 | 8/2017 | Yang et al. |
| 2017/0238951 A1 | 8/2017 | Yang et al. |
| 2017/0238953 A1 | 8/2017 | Yang et al. |
| 2017/0246014 A1 | 8/2017 | Rapaport et al. |
| 2017/0252057 A1* | 9/2017 | Bonnette ........ A61B 17/32037 |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |
| 2018/0193026 A1 | 7/2018 | Yang |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer |
| 2018/0242962 A1 | 8/2018 | Walen et al. |
| 2018/0242980 A1 | 8/2018 | Lubock |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |

(56) References Cited

U.S. PATENT DOCUMENTS

| | | |
|---|---|---|
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0353194 A1 | 12/2018 | Shaffer et al. |
| 2019/0022363 A1 | 1/2019 | Grayzel et al. |
| 2019/0029825 A1 | 1/2019 | Fitterer et al. |
| 2019/0070387 A1 | 3/2019 | Goyal |
| 2019/0108540 A1 | 4/2019 | Look et al. |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0336149 A1 | 11/2019 | Yang |
| 2019/0336727 A1 | 11/2019 | Yang |
| 2019/0351182 A1 | 11/2019 | Chou et al. |
| 2019/0366041 A1 | 12/2019 | Yang |
| 2020/0001046 A1 | 1/2020 | Yang |
| 2020/0008820 A1 | 1/2020 | Aboytes et al. |
| 2020/0009350 A1 | 1/2020 | Goyal |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0046937 A1 | 2/2020 | Nakagawa et al. |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0188630 A1 | 6/2020 | Fujita et al. |
| 2020/0025845 A1 | 7/2020 | Yang et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297362 A1 | 9/2020 | Deville et al. |
| 2020/0297972 A1 | 9/2020 | Yee |
| 2020/0306501 A1 | 10/2020 | Yee |
| 2020/0323535 A1 | 10/2020 | Yang |
| 2020/0337716 A1 | 10/2020 | Garrison et al. |
| 2020/0345979 A1 | 11/2020 | Loh et al. |
| 2021/0001141 A1 | 1/2021 | Pfiffner et al. |
| 2021/0045758 A1 | 2/2021 | Garrison et al. |
| 2021/0052296 A1 | 2/2021 | Garrison |
| 2021/0068852 A1 | 3/2021 | Spence |
| 2021/0093336 A1 | 4/2021 | Roue |
| 2021/0106238 A1 | 4/2021 | Strasser |
| 2021/0106792 A1 | 4/2021 | Rafiee |
| 2021/0128182 A1 | 5/2021 | Teigen et al. |
| 2021/0146094 A1 | 5/2021 | Christian et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0315596 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |
| 2021/0361909 A1 | 11/2021 | Cottone et al. |
| 2021/0378527 A1 | 12/2021 | Strasser et al. |
| 2021/0378696 A1 | 12/2021 | Yang et al. |
| 2022/0047849 A1 | 2/2022 | Yee et al. |

FOREIGN PATENT DOCUMENTS

| | | |
|---|---|---|
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 349 486 | 3/2008 |
| EP | 2 069 528 | 3/2013 |
| EP | 2 937 108 | 10/2015 |
| EP | 2 928 360 | 1/2017 |
| EP | 2 211 732 | 5/2018 |
| EP | 3 539 486 | 9/2019 |
| EP | 3 698 740 | 8/2020 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2009/054968 | 4/2009 |
| WO | WO 2009/132218 | 10/2009 |
| WO | WO 2010/126786 | 11/2010 |
| WO | WO 2014/151209 | 9/2014 |
| WO | WO 2014/203336 | 12/2014 |
| WO | WO 2017/025775 | 2/2017 |
| WO | WO 2018/121363 | 7/2018 |
| WO | WO 2019/178165 | 9/2019 |
| WO | WO 2019/222518 | 11/2019 |
| WO | WO 2019/246583 | 12/2019 |
| WO | WO 2020/145928 | 7/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/242734 | 12/2021 |

OTHER PUBLICATIONS

U.S. Appl. No. 15/443,838 (U.S. Pat. No. 10,179,224), filed Feb. 27, 2017, Enhanced Flexibility Neurovascular Catheter With Tensile Support.

U.S. Appl. No. 15/443,877 (U.S. Pat. No. 10,183,146), filed Feb. 27, 2017, Method of Making an Enhanced Flexibility Neurovascular Catheter.

U.S. Appl. No. 15/443,948 (U.S. Pat. No. 10,441,745), filed Feb. 27, 2017, Neurovascular Catheter With Enlargeable Distal End.

U.S. Appl. No. 16/542,657, filed Aug. 16, 2019, Method of Making an Enhanced Flexibility Neurovascular Catheter.

U.S. Appl. No. 15/444,038 (U.S. Pat. No. 10,183,147), filed Feb. 27, 2017, Neurovascular Catheter Extension Segment.

U.S. Appl. No. 16/398,626 (U.S. Pat. No. 10,835,272), filed Apr. 30, 2019 (Nov. 17, 2020). Devices and Methods for Removing Obstructive From an Intravascular Material.

U.S. Appl. No. 16/400,263, filed May 1, 2019, Neurovascular Catheter Having Atraumatic Angled Tip.

U.S. Appl. No. 16/570,084, filed Sep. 13, 2019, Enhanced Flexibility Neurovascular Catheter With Tensile Support.

U.S. Appl. No. 16/683,718 (U.S. Pat. No. 10,653,434), filed Nov. 14, 2019, Devices and Methods for Removing Obstructive Material From an Intravascular Site.

U.S. Appl. No. 17/070,832, filed Oct. 14, 2020, Systems and Methods for Multivariate Stroke Detection.

U.S. Appl. No. 17/125,723, filed Dec. 7, 2020, Methods and Systems for Advancing a Catheter to a Target Site.

U.S. Appl. No. 17/125,743, filed Dec. 17, 2020, Systems for Accessing a Central Pulmonary Artery.

U.S. Appl. No. 15/862,488 (U.S. Pat. No. 10,653,426), filed Jan. 4, 2018, Thromboresistant Coatings for Aneurysm Treatment Devices.

U.S. Appl. No. 16/863,723, filed Apr. 30, 2020, Thromboresistant Coatings for Aneurysm Treatment Devices.

U.S. Appl. No. 15/442,393 (U.S. Pat. No. 10,183,145), filed Feb. 24, 2017, Enhanced Flexibility Neurovascular Catheter.

U.S. Appl. No. 15/443,874, filed Feb. 27, 2017, Telescoping Neurovascular Catheter With Enlargeable Distal Opening.

U.S. Appl. No. 16/398,626, filed Apr. 30, 2019, Devices and Methods for Removing Obstructive Material Removing From an Intravascular Site.

U.S. Appl. No. 16/683,718 (U.S. Pat. No. 10,653,434), filed Nov. 14, 2019, Devices and Methods for Removing Obstructive Material Removing From an Intravascular Site.

(56) References Cited

OTHER PUBLICATIONS

U.S. Appl. No. 16/589,563, filed Oct. 1, 2019, Devices and Methods for Removing Obstructive Material Removing From an Intravascular Site.
U.S. Appl. No. 15/443,948 (U.S. Pat. No. 10,441,745), filed Feb. 27, 2017 (Jan. 22, 2019), Neurovascular Catheter With Enlargeable Distal End.
U.S. Appl. No. 17/357,558, filed Jun. 24, 2021, Aspiration System With Accelerated Response.
U.S. Appl. No. 17/343,004, filed Jun. 9, 2021, Catheter With Enhanced Tensile Strength.
Guidezilla Guide Extension Catheter, Boston Scientific 510k Submission, Feb. 20, 2017.
Merit Medical Systems Acquired Distal Access's SPINR Platform, Jul. 15, 2015, Digital Access, LLC; Merit Medical Systems, 5 pages.
Simon et al., Exploring the efficacy of cyclic vs. static aspiration in a cerebral thrombectomy model: an initial proof of concept study, J. NeuroInvent Surg 2014, 6 pp. 677-683.
Simon et al., Hydrodynamic comparison of the Penumbra system and commonly available syringes in forced—suction thrombectomy, J. NeuroInvent Surg 2014, 6, pp. 205-211.
Spiotta et al., Evolution of thrombectomy approaches and devices for acute stroke: a technical review, J. Neuro Intervent Surg 2015, 7, pp. 2-7.
U.S. Appl. No. 16/683,718 (U.S. Pat. No. 10,653,434), filed Nov. 14, 2019, Devices and Methods for Removing Obstructive From an Intravascular Material.
U.S. Appl. No. 16/589,563, filed Oct. 1, 2019, Devices and Methods for Removing Obstructive From an Intravascular Material.
U.S. Appl. No. 17/125,723, filed Dec. 17, 2020, Methods and Systems for Advancing a Catheter to a Target Site.
U.S. Appl. No. 15/862,488, Thromboresistant Coatings for Aneurysm Treatment Devices, filed Jan. 4, 2018.
U.S. Appl. No. 15/442,393 (U.S. Pat. No. 10,183,145), Enhanced Flexibility Neurovascular Catheter, filed Feb. 24, 2017 (Jan. 22, 2019).
U.S. Appl. No. 15/443,874, Telescoping Neurovascular Catheter With Enlargeable Distal Opening, filed Feb. 27, 2017.
U.S. Appl. No. 15/443,841, Method of Pulsatile Neurovascular Aspiration With Telescoping Catheter, filed Feb. 27, 2017.
U.S. Appl. No. 15/443,838 (U.S. Pat. No. 10,179,224), Enhanced Flexibility Neurovascular Catheter With Tensile Support, filed Feb. 27, 2017 (Jan. 15, 2019).
U.S. Appl. No. 15/443,877 (U.S. Pat. No. 10,183,146), Method of Making an Enhanced Flexibility Neurovascular Catheter, filed Feb. 27, 2017 (Jan. 22, 2019).
U.S. Appl. No. 15/443,948, Neurovascular Catheter With Enlargeable Distal End, filed Feb. 27, 2017.
U.S. Appl. No. 16/542,657, Method of Making an Enhanced Flexibility Neurovascular Catheter, filed Aug. 16, 2019.
U.S. Appl. No. 15/444,038 (U.S. Pat. No. 10,183,147), Neurovascular Catheter Extension Segment, filed Feb. 27, 2017 (Jan. 22, 2019).
U.S. Appl. No. 16/503,899, Sealed Neurovascular Extendable Catheter, filed Jul. 5, 2019.
U.S. Appl. No. 16/398,626, Devices and Methods for Removing Obstructive Material From an Intravascular Site, filed Apr. 30, 2019.
U.S. Appl. No. 16/400,263, Neurovascular Catheter Having Atraumatic Angled Tip, filed May 1, 2019.
U.S. Appl. No. 16/570,084, Enhanced Flexibility Neurovascular Catheter With Tensile Support, filed Sep. 13, 2019.
Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.
U.S. Appl. No. 17/125,742, filed Dec. 17, 2020, Accessing and Retrieving for Accessing and Retrieving Thrombo-Emboli.
Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.
Korpelainen et al., 1995, Asymmetrical skin temperature in ischemic stroke, Stroke, 26(9):1543-1547.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 16/863,723 (U.S. Pat. No. 11,224,434), filed Apr. 30, 2020 (Jan. 18, 2022), Thromboresistant Coatings for Aneurysm Treatment Devices.
U.S. Appl. No. 17/574,907, filed Jan. 13, 2022, Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having Atraumatic Angled Tip.
U.S. Appl. No. 16/570,084 (U.S. Pat. No. 11,311,303), filed Sep. 13, 2019 (Apr. 26, 2022), Enhanced Flexibility Neurovascular Catheter With Tensile Support.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 17/410,162, filed Aug. 24, 2021, Neurovascular Catheter Having Angled Tip.
U.S. Appl. No. 16/589,563, filed Oct. 1, 2019, Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832 (U.S. Pat. No. 11,134,859), filed Oct. 14, 2020 (Oct. 5, 2021), Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723 (U.S. Pat. No. 11,065,018), filed Dec. 17, 2020 (Jul. 20, 2021), Methods and Systems for Advancing a Catheter to a Target Site.

(56) References Cited

OTHER PUBLICATIONS

U.S. Appl. No. 17/125,217, filed Dec. 17, 2020, Methods and Systems for Treating a Pulmonary Embolism.
U.S. Appl. No. 17/125,743 (U.S. Pat. No. 11,253,277), filed Dec. 17, 2020 (Feb. 22, 2022), Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboembolic Disease.
U.S. Appl. No. 17/357,558 (U.S. Pat. No. 11,259,821), filed Jun. 24, 2021 (Mar. 1, 2022), Aspiration System With Accelerated Response.
U.S. Appl. No. 17/357,643, filed Jun. 24, 2021, Hemostasis Valve.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/475,202, filed Sep. 14, 2021, Enhanced Flexibility Neurovascular Catheter.
U.S. Appl. No. 17/343,004 (U.S. Pat. No. 11,207,497), filed Jun. 9, 2021 (Dec. 28, 2021), Catheter With Enhanced Tensile Strength.
U.S. Appl. No. 17/398,244, filed Aug. 10, 2021, Catheter With a Preset Curve.
U.S. Appl. No. 29/811,884, filed Oct. 18, 2021, Inline Fluid Filter.
U.S. Appl. No. 17/527,393, filed Nov. 16, 2021, Catheter Drive System for Supra-Aortic Access.
U.S. Appl. No. 17/527,379, filed Nov. 16, 2021, Rob Otically Driven Interventional Device.
U.S. Appl. No. 17/527,460, filed Nov. 16, 2021, Sterile Packaging Assembly for Robotic Interventional Device.
U.S. Appl. No. 17/527,452, filed Nov. 16, 2021, Method of Robotically Performing a Neurovascular Procedure.
U.S. Appl. No. 17/527,456, filed Nov. 16, 2021, Multi Catheter Method of Performing a Robotic Neurovascular Procedure.

* cited by examiner

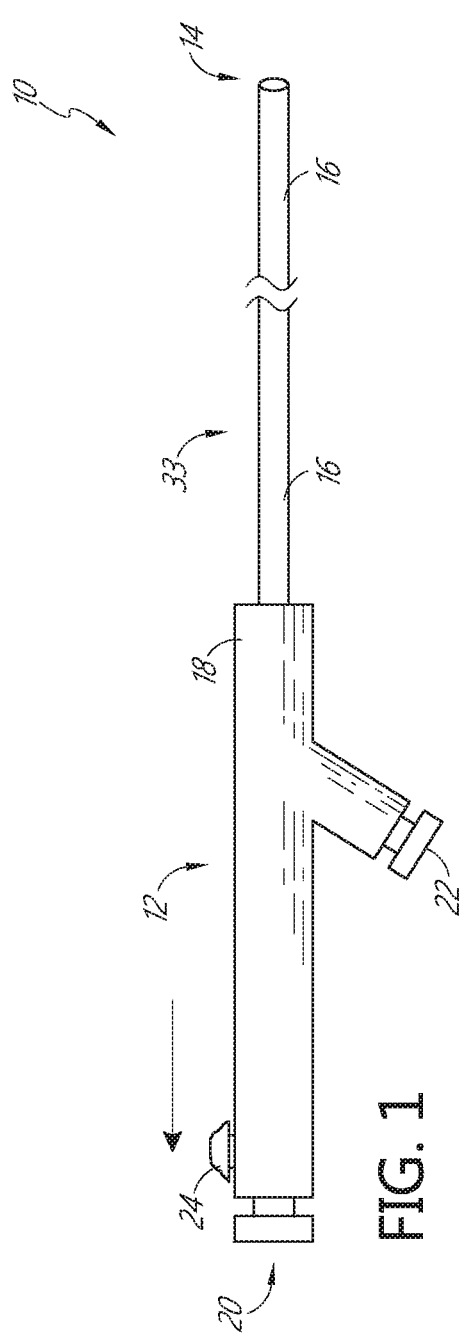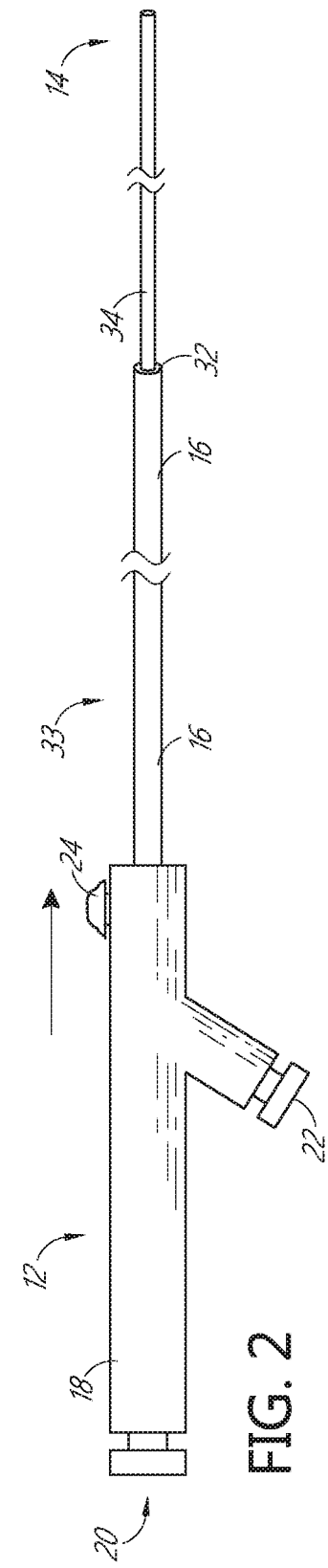

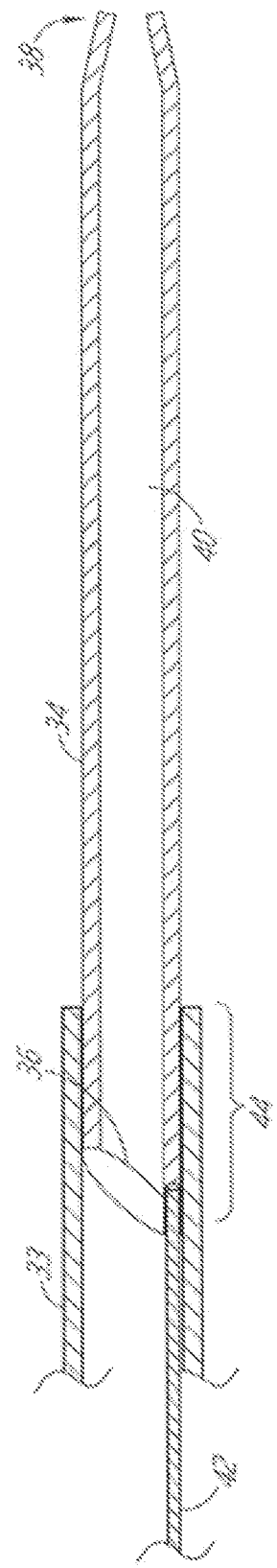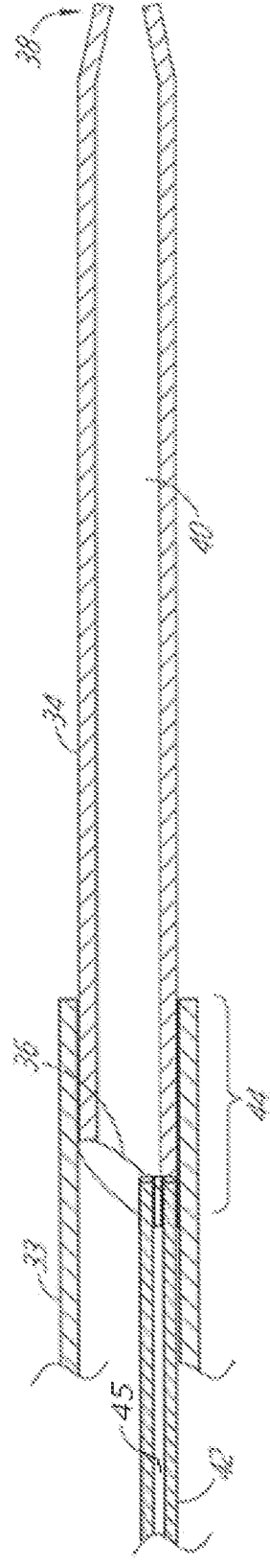

VACUUM TRANSFER TOOL FOR EXTENDABLE CATHETER

CROSS-REFERENCE TO RELATED APPLICATIONS

This application claims the benefit of U.S. Provisional Application No. 62/694,792, filed Jul. 6, 2018, the entirety of this application is hereby incorporated by reference herein.

BACKGROUND

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons or stents have been used to create a patent lumen through the clot when clot removal or dissolution was not possible.

Notwithstanding the foregoing, there remains a need for new devices and methods for treating vasculature occlusions in the body, including acute ischemic stroke and occlusive cerebrovascular disease.

SUMMARY

There is provided in according with one aspect, a telescoping catheter, comprising: an elongate, flexible tubular body, comprising a proximal section having at least one lumen and a distal section axially movably positioned within the lumen; and a control for advancing the distal section from a first, proximally retracted position within the proximal section to a second, extended position, extending distally beyond the proximal section; and an active tip on the distal end of the distal section, comprising a distal opening that is movable between a smaller and a larger configuration.

In one aspect of present disclosure, the control comprises a pull wire extending through the proximal section. In another aspect of present disclosure, the distal section is distally advanceable to extend beyond the proximal section for a distance of at least about 10 cm. In yet another aspect of present disclosure, the distal section is distally advanceable to extend beyond the proximal section for a distance of at least about 25 cm.

In one aspect of present disclosure, the distal opening is movable in response to movement of a control wire. In another aspect of present disclosure, the distal opening is movable between a smaller and a larger configuration in response to application of vacuum to the lumen. In yet another aspect of present disclosure, the size of the distal opening is changed by lateral movement of a side wall on the distal section. In yet another aspect of present disclosure, the distal opening comprises at least one movable jaw. In another aspect of present disclosure, the distal end of the distal section comprises a duck bill valve configuration.

In one aspect of present disclosure, the telescoping catheter may further comprise a controller for applying intermittent vacuum to the lumen. The controller may be configured to apply pulses of vacuum to the lumen spaced apart by spaces of neutral pressure. The controller may be configured to alternate between applying pulses of higher negative pressure and lower negative pressure. The distal tip of the catheter may axially reciprocate in response to application of pulses of vacuum to the lumen.

In another aspect of the present disclosure, disclosed herein is a vacuum transfer tool for maintaining a vacuum within an extendable catheter. The vacuum transfer tool has a proximal transfer tube and a distal transfer tube. The proximal transfer tube has a proximal end, a distal end, a lumen extending from the proximal end to the distal end, and an aspiration port in fluid communication with the lumen. The aspiration port is positioned between the proximal end and the distal end. The distal transfer tube has a proximal end, a distal end, a lumen extending from the proximal end to the distal end, and an aspiration port in fluid communication with the lumen. The aspiration port is positioned between the proximal end and the distal end. The distal end of the proximal transfer tube is removably connectable to the proximal end of the distal transfer tube. The distal end of the distal transfer tube is directly or indirectly connectable to a proximal end of a catheter. The proximal end of the proximal transfer tube has a proximal sealing port configured to receive and form a fluid seal around an extendable catheter segment. The proximal transfer tube is configured to form a sealed space between the proximal end and the distal end of the proximal transfer tube around the extendable catheter segment. The distal transfer tube is configured to receive the extendable catheter segment from the proximal transfer tube and to position the extendable catheter segment within a lumen of the catheter.

The proximal end of the distal transfer tube may have a fluid sealing port. The fluid sealing port may be a self-sealing port. The distal transfer tube may be removably connectable directly or indirectly to the proximal end of the catheter. The distal end of the proximal transfer tube may have an introducer configured to be received within the lumen of the distal transfer tube. The introducer may have a rigid tubular body. The introducer may have a step adjacent the rigid tubular body, the step being configured to abut the proximal end of the distal transfer tube. The proximal sealing support of the proximal transfer tube may be a rotating hemostasis valve. The proximal transfer tube may have a rotating hemostasis valve between the introducer and the aspiration port configured to help form the sealed space. The proximal transfer tube may have two rotating hemostasis valves positioned on opposite sides of the aspiration port. The rotating hemostasis valves may be configured to form the sealed space when closed. The rotating hemostasis valves may be configured to secure the extendable catheter segment to the proximal transfer tube when closed such that movement of the proximal transfer tube simultaneously moves the extendable catheter segment.

At least portions of the proximal transfer tube and/or the distal transfer tube may be transparent. The proximal transfer tube may be configured to allow visual determination of the positioning of the proximal end of the extendable catheter segment within a portion of the lumen corresponding to the sealed space. The vacuum transfer tool may further include the catheter. The vacuum transfer tool may further include the extendable catheter segment.

In another aspect of the present disclosure, disclosed herein is a method of aspirating a clot from a blood vessel using an extendable catheter. The method includes introducing a catheter into the blood vessel, coupling a proximal transfer tube to a distal transfer tube, inserting an extendable catheter segment through the proximal transfer tube and into the distal transfer tube, and inserting the extendable catheter segment through the distal transfer tube and into the catheter. The proximal transfer tube has a proximal end, a distal end, a lumen extending from the proximal end to the distal end, and an aspiration port in fluid communication with the lumen. The aspiration port is positioned between the proximal end and the distal end. The distal transfer tube has a proximal end, a distal end, a lumen extending from the proximal end to the distal end, and an aspiration port in fluid communication with the lumen. The aspiration port is positioned between the proximal end and the distal end. The proximal transfer tube is attached or attachable to a proximal end of the catheter. The method further includes retracting the extendable catheter segment while aspiration is provided by both the aspiration port of the proximal transfer tube and the aspiration port of the distal transfer tube. The method further includes positioning the proximal end of the extendable catheter segment within a portion of the proximal transfer tube corresponding to a sealable space and sealing the sealable space of the proximal transfer tube such that a vacuum is maintained by the aspiration port of the proximal transfer tube around the proximal end of the extendable catheter segment. The method further includes withdrawing the extendable catheter segment from the distal transfer tube by decoupling the proximal transfer tube and the distal transfer tube and moving the proximal transfer tube away from the distal transfer tube while maintaining a vacuum within the distal transfer tube via the aspiration port of the distal transfer tube.

The method may include extending the extendable catheter segment such that a distal end of the extendable catheter segment extends distally beyond a distal end of the catheter. The method may include attaching the distal end of the distal transfer tube directly or indirectly to the proximal end of the catheter. The method may include capturing the clot on the distal end of the extendable catheter segment prior to retracting the extendable catheter segment. The method may include transferring the clot from the distal end of the extendable catheter segment. The method may include applying an irrigation fluid to at least one of the aspiration port of the proximal transfer tube and the aspiration port of the distal transfer tube. Sealing the sealable space may comprise rotating a rotating hemostasis valve proximal to the aspiration port and rotating a rotating hemostasis valve distal to the aspiration port. Sealing the sealable space may secure the extendable catheter segment to the proximal transfer tube such that the extendable transfer segment is not axially translatable relative to the proximal transfer tube.

The method may include closing a fluid sealing port on the proximal end of the proximal transfer tube around a pull wire to a first position, extending the extendable catheter segment through the catheter while the fluid sealing port is in the first position, retracting the extendable catheter segment through the catheter while the fluid sealing port is in the first position, and further closing the fluid sealing port around the pull wire to a second position. The pull wire may be connected to the extendable catheter segment. The first position may form a fluid seal around the pull wire but allow axial translation of the pull wire through the proximal sealing port. The second position may form a better fluid seal around the pull wire than the first position and disallow axial translation of the pull wire through the proximal sealing port. The withdrawing of the extendable catheter segment from the distal transfer tube may be performed while the proximal sealing port is in the second position.

The method may include inserting an agitator through the proximal transfer tube after the extendable catheter segment is withdrawn. The method may include inserting an agitator through a central lumen in the pull wire while the pull wire extends through the proximal transfer tube.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

FIG. 1 is a side elevational schematic view of an intracranial aspiration catheter in accordance with the present invention, with a distal segment in a proximally retracted configuration.

FIG. 2 is a side elevational view as in FIG. 1, with the distal segment in a distally extended configuration.

FIGS. 3A-3B are cross-sectional elevational views of a distal end of catheter 10, with the distal section 34 fully extended.

FIG. 14A shows the vacuum transfer device comprising the proximal transfer tube uncoupled from the distal transfer tube. FIG. 14B shows the distal transfer tube. FIG. 14C shows the proximal transfer tube.

DETAILED DESCRIPTION

Figure 4:
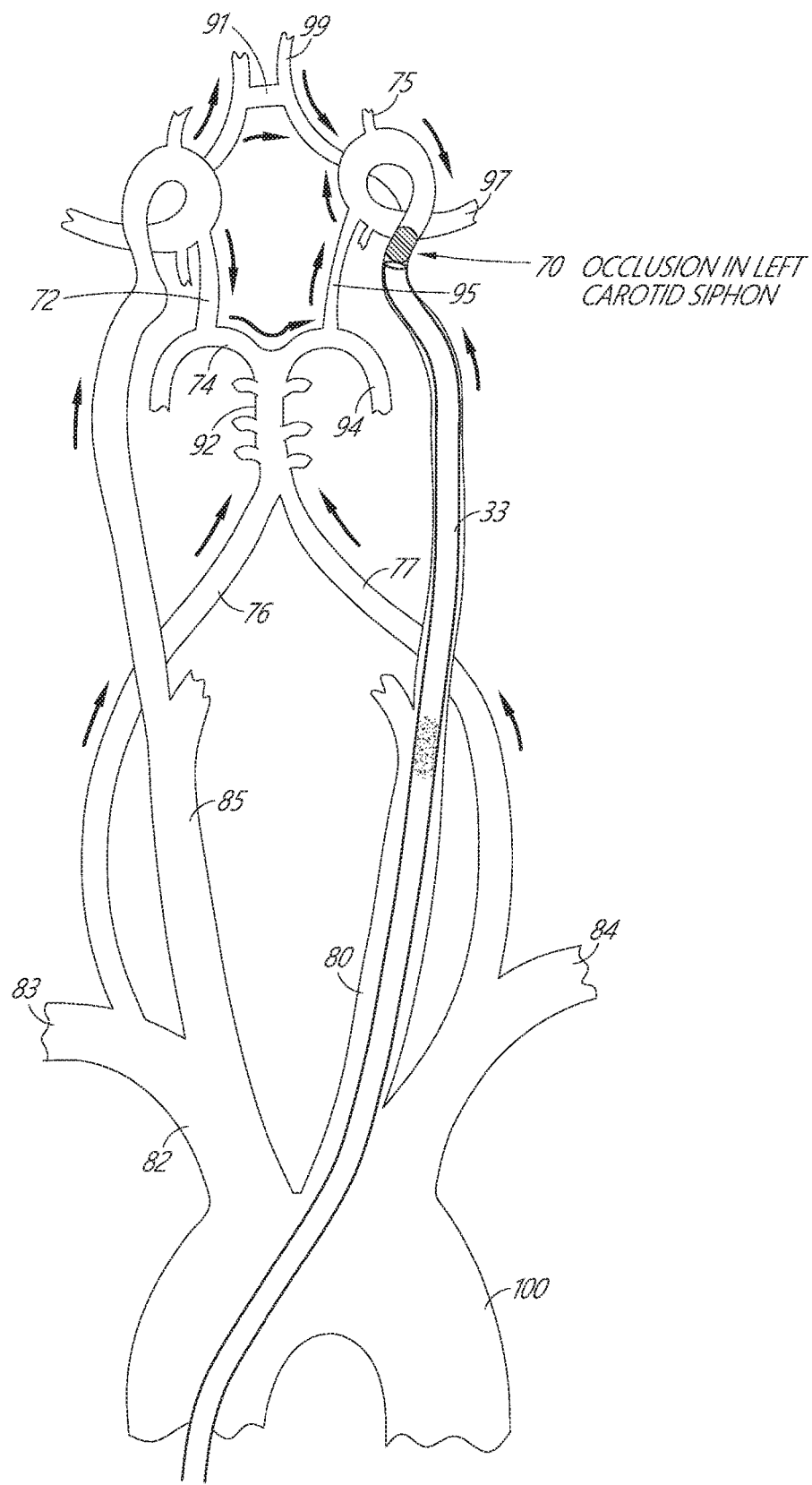
FIG. 4 depicts cerebral arterial vasculature including the Circle of Willis, and an access catheter positioned at an occlusion in the left carotid siphon artery.

Referring to FIG. 1, there is disclosed a catheter 10 in accordance with one aspect of the present invention. Although primarily described in the context of an axially extendable distal segment aspiration catheter with a single central lumen, catheters of the present invention can readily be modified to incorporate additional structures, such as permanent or removable column strength enhancing mandrels, two or more lumen such as to permit drug, contrast or irrigant infusion or to supply inflation media to an inflatable balloon carried by the catheter, or combinations of these features, as will be readily apparent to one of skill in the art in view of the disclosure herein. In addition, the present invention will be described primarily in the context of removing obstructive material from remote vasculature in the brain, but has applicability as an access catheter for delivery and removal of any of a variety of diagnostics or therapeutic devices with or without aspiration.

The catheters disclosed herein may readily be adapted for use throughout the body wherever it may be desirable to distally advance a low profile distal catheter segment from a larger diameter proximal segment. For example, axially extendable catheter shafts in accordance with the present invention may be dimensioned for use throughout the coronary and peripheral vasculature, the gastrointestinal tract, the urethra, ureters, Fallopian tubes and other lumens and potential lumens, as well. The telescoping structure of the present invention may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

In the illustrated embodiment, the tubular body 16 is divided into at least a fixed proximal section 33 and an axially extendable and retractable distal section 34 separated at a transition 32. FIG. 2 is a side elevational view of the catheter 10 shown in FIG. 1, with the distal segment in a distally extended configuration.

Referring to FIGS. 3A and 3B, there is illustrated a cross-sectional view of the distal segment 34 shown extended distally from the proximal segment 33 in accordance with the present invention. Distal segment 34 extends between a proximal end 36 and a distal end 38 and defines at least one elongate central lumen 40 extending axially therethrough. Distal end 38 may be provided with one or more movable side walls or jaws 39, which move laterally in the direction of an opposing side wall or jaw 41 under the influence of aspiration, to enable the distal end 38 to bite or break thrombus or other material into smaller particles, to facilitate aspiration through lumen 40. Both walls 39 and 41 may be movable towards and away from each other to break up thrombus as is discussed further below. For certain applications, the proximal section 33 may also or alternatively be provided with one or two opposing jaws, also responsive to vacuum or mechanical actuation to break up thrombus.

The inner diameter of the distal section 34 may be between about 0.030 inches and about 0.112 inches, between about 0.040 inches and about 0.102 inches, between about 0.045 inches and about 0.097 inches, between about 0.050 inches and about 0.092 inches, between about 0.055 inches and about 0.087 inches, between about 0.060 inches and about 0.082 inches, between about 0.062 inches and about 0.080 inches, between about 0.064 inches and about 0.078 inches, between about 0.066 inches and about 0.076 inches, between about 0.068 inches and about 0.074 inches, or between about 0.070 inches and about 0.072 inches.

The inner diameter and the outer diameter of the distal section 34 may be constant or substantially constant along its longitudinal length. The inner diameter may be at least about 0.06 inches, 0.065 inches, 0.07 inches, 0.075 inches, 0.08 inches, or more than 0.08 inches. The outer diameter may be at least about 0.07 inches, 0.075 inches, 0.08 inches, 0.085 inches, 0.09 inches, 0.095 inches, 0.1 inches, or more than 0.1 inches. The total thickness of the sidewall extending between the inner and outer diameter may be at least about 0.005 inches, 0.010 inches, 0.015 inches, 0.02 inches, 0.025 inches, or more than 0.025 inches. For example, the distal section may 34 may have an inner diameter of about 0.071 inches and an outer diameter of about 0.083 inches. Alternatively, the distal section 34 may be tapered near its distal end. A larger lumen (internal diameter) may increase the applied aspiration force through the distal end of the distal section 34. A smaller outer diameter may provide better catheter trackability and/or may better enable the catheter to reach more distal anatomy (e.g. neuroanatomy), as the tapered distal end may be better accommodated in smaller blood vessels. The inner and outer diameters of the distal section 34 may be correlated in order to maintain a sufficient sidewall thickness that provides sufficient structural integrity to the catheter. The distal section 34 may be tapered at less than or equal to about 5 cm, about 10 cm, about 15 cm, about 20 cm, about 23 cm, about 25 cm, about 30 cm, about 31 cm, about 35 cm, about 40 cm, about 45 cm, about 50 cm, about 60 cm, or about 70 cm from its distal end. In some embodiments, the taper may be positioned between about 25 cm and about 35 cm from the distal end of the distal section 34.

The inner diameter of the distal section 34 may be tapered or decreased in the distal direction near the distal end to an internal diameter that is less than or equal to about 95%, about 90%, about 85%, about 80%, about 75%, about 70%, about 65%, about 60%, about 55%, or about 50% of the adjacent, untapered internal diameter. In some embodiments, the internal diameter of the tapered distal section 34 may be between about 50% and about 70% of the adjacent, untapered internal diameter. For example, the untapered internal diameter at the proximal end of the distal section 34 may be about 0.071 inches and the tapered internal diameter at the distal end of the distal section 34 may be about 0.035 inches, 0.045 inches, or 0.055 inches. The inner diameter of the distal section 34 may be tapered or increased near the distal end by greater than or equal to about 102%, 104%, 106%, 108%, or more of the internal diameter just proximal to a transition into the taper. The tapered inner diameter of the distal section 34 may be less than or equal to about 0.11 inches, about 0.1 inches, about 0.090 inches, about 0.080 inches, about 0.070 inches, about 0.065 inches, about 0.060 inches, about 0.055 inches, about 0.050 inches, about 0.045 inches, about 0.040 inches, about 0.035 inches, about 0.030 inches, about 0.025 inches, about 0.020 inches, about 0.015 inches, or about 0.010 inches. The taper in the outer diameter of the tapered portion of the distal section 34 may be matched to maintain a constant thickness of the sidewall. Alternatively, the sidewall may be thinner along the tapered portion. For instance, the sidewall may be no greater than 95%, 90%, 85%, 80%, 75%, 70%, or less than 70% of the thickness of the sidewall along the proximal portion of the distal section 34. In some embodiments, the length of the distal tapered portion of the distal section 34 may be between about 25 cm and about 35 cm, between about 25 cm and about 30 cm, between about 30 cm and 35 cm, or approximately 30 cm.

In some embodiments, the proximal segment 33 may have an inner diameter of at least about 0.07 inches, 0.075 inches, 0.08 inches, 0.085 inches, 0.09 inches, 0.1 inches, 0.105 inches, or more than 0.105 inches. The proximal segment 33 may have an outer diameter of at least about 0.08 inches, 0.085 inches, 0.09 inches, 0.095 inches, 0.01 inches, 0.105 inches, 0.11 inches, 0.0115 inches, 0.012 inches, or more than 0.012 inches. For example, the inner diameter may be approximately 0.088 inches and the outer diameter may be approximately 0.106 inches. The sidewall of the proximal segment 33 may have a thickness of at least about 0.005 inches, 0.01 inches, 0.015 inches, 0.02 inches, 0.025 inches, or more than 0.25 inches. In some embodiments, the proximal segment 33 has a constant inner and/or outer diameter along its length. In some embodiments, the proximal segment 33 may slightly taper or decrease in diameter along the distal direction. For example, in some embodiments, the outer diameter of the proximal segment 33 may be about 0.106 inches at the distal end and about 0.108 inches at the proximal end.

The length of the proximal segment 33 may be at least about 90 cm, 95 cm, 100 cm, 105 cm, 110 cm, 115 cm, 120 cm, 125 cm, 130 cm, 135 cm, or more than 135 cm. For example, in one embodiment the length is approximately 106 cm. In another embodiment, the length is approximately 117 cm. In some neurovascular applications, the distal end of the proximal segment 33 may extend at least to the Horizontal Petrous segment of the vasculature.

In some embodiments, the length of the distal section 34 may be between about 13 cm and about 53 cm, between about 18 cm and about 48 cm, between about 23 cm and about 43 cm, between about 28 cm and about 38 cm, between about 20 cm and 30 cm, or between about 25 cm and 30 cm. The length of the distal section 34 may be less than or equal to about 20 cm, about 25 cm, about 30 cm, about 33 cm, about 35 cm, about 40 cm, about 41 cm, about 45 cm, about 50 cm, about 55 cm, about 60 cm, about 70 cm, or about 80 cm. The length of the distal section 34 may depend on the degree of tapering of the internal diameter of the distal section 34.

The inner diameter and the outer diameter of the distal section 34 may be constant or substantially constant along its longitudinal length. The inner diameter may be at least about 0.06 inches, 0.065 inches, 0.07 inches, 0.075 inches, 0.08 inches, or more than 0.08 inches. The outer diameter may be at least about 0.07 inches, 0.075 inches, 0.08 inches, 0.085 inches, 0.09 inches, 0.095 inches, 0.1 inches, or more than 0.1 inches. The total thickness of the sidewall extending between the inner and outer diameter may be at least about 0.005 inches, 0.010 inches, 0.015 inches, 0.02 inches, 0.025 inches, or more than 0.025 inches. For example, the distal section may 34 may have an inner diameter of about 0.071 inches and an outer diameter of about 0.083 inches. Alternatively, the distal section 34 may be tapered near its distal end. A larger lumen (internal diameter) may increase the applied aspiration force through the distal end of the distal section 34. A smaller outer diameter may provide better catheter trackability and/or may better enable the catheter to reach more distal anatomy (e.g. neuroanatomy), as the tapered distal end may be better accommodated in smaller blood vessels. The inner and outer diameters of the distal section 34 may be correlated in order to maintain a sufficient sidewall thickness that provides sufficient structural integrity to the catheter. The distal section 34 may be tapered at less than or equal to about 5 cm, about 10 cm, about 15 cm, about 20 cm, about 23 cm, about 25 cm, about 30 cm, about 31 cm, about 35 cm, about 40 cm, about 45 cm, about 50 cm, about 60 cm, or about 70 cm from its distal end.

The inner diameter of the distal section 34 may be tapered or decreased near the distal end by less than or equal to about 95%, about 90%, about 85%, about 80%, about 75%, about 70%, about 65%, about 60%, about 55%, about 50%, about 45%, about 40%, about 35%, about 30%, about 25%, about 20%, about 10%, or about 5%. The inner diameter of the distal section 34 may be tapered or decreased near the distal end by greater than or equal to about 95%, about 90%, about 85%, about 80%, about 75%, about 70%, about 65%, about 60%, about 55%, about 50%, about 45%, about 40%, about 35%, about 30%, about 25%, about 20%, about 10%, or about 5%. The tapered inner diameter of the distal section 34 may be by less than or equal to about 0.11 inches, about 0.1 inches, about 0.090 inches, about 0.080 inches, about 0.070 inches, about 0.065 inches, about 0.060 inches, about 0.055 inches, about 0.050 inches, about 0.045 inches, about 0.040 inches, about 0.035 inches, about 0.030 inches, about 0.025 inches, about 0.020 inches, about 0.015 inches, or about 0.010 inches.

The length of the distal section 34 may be between about 13 cm and about 53 cm, between about 18 cm and about 48 cm, between about 23 cm and about 43 cm, or between about 28 cm and about 38 cm. The length of the distal section 34 may be less than or equal to about 20 cm, about 25 cm, about 30 cm, about 33 cm, about 35 cm, about 40 cm, about 41 cm, about 45 cm, about 50 cm, about 55 cm, about 60 cm, about 70 cm, or about 80 cm. The length of the distal section 34 may depend on the degree of tapering of the internal diameter of the distal section 34.

The proximal end 36 of distal section 34 is provided with a proximally extending pull wire 42. Pull wire 42 extends proximally throughout the length of the tubular body 16, to control 24 which may be carried by manifold 18. Axial movement of control 24 produces a corresponding axial movement of distal section 34 with respect to proximal section 33 as has been discussed. Alternatively, the proximal end of pull wire 42 may exit through a port on manifold 18, such that it may be manually grasped and pulled or pushed by the clinician to extend or retract the distal section 34. The length of the pull wire 42 may be between about 700 mm and about 1556 mm, between about 800 mm and about 1456 mm, between about 850 mm and about 1406 mm, between about 900 mm and about 1356 mm, between about 950 mm and about 1306 mm, between about 1000 mm and about 1256 mm, between about 1020 mm and about 1236 mm, between about 1040 mm and about 1216 mm, between about 1060 mm and about 1196 mm, between about 1080 mm and about 1176 mm, between about 1100 mm and about 1156 mm, between about 1110 mm and about 1146 mm, or between about 1120 mm and about 1136 mm. In some preferred embodiments, the length of the pull wire 42 may be between approximately 110-120 cm.

Upon distal advance of pull wire 42 to its limit of travel, an overlap 44 remains between the proximal end 36 of distal section 34 and the proximal section 33. This overlap 44 is configured to provide a seal to enable efficient transmission of vacuum from proximal section 33 to distal section 34. In some embodiments, the length of the pull wire 42 may be limited to ensure that there is a minimal overlap 44 between the proximal segment 33 and the distal segment 34 when the pull wire 42 is fully inserted into the proximal segment 33 or attached manifold in a distal direction. In some embodiments, the length of the proximal segment 33 may be sufficiently long for neurovascular applications such that when the proximal segment is positioned in a relatively proximal position (e.g., the horizontal petrous segment), the neuroanatomy effectively limits the distance by which the distal segment 34 may be extended, ensuring a sufficient overlap 44. For example, the distal segment 34 may not be able to extend further than the M2 segment of the middle cerebral artery (MCA) given its dimensions. Overlap 44 may be provided with any of a variety of additional features to facilitate a seal, such as a gasket, coating or tightly toleranced sliding fit, as described elsewhere herein. In some embodiments, the proximal end of the distal segment 34 may be slightly expanded to create a seal. For instance, the outer diameter of the proximal end of the distal segment 34 and the inner diameter of the proximal segment 33 may both be about 0.088 inches. Preferably the clearance between the OD of the distal section 34 and ID of the proximal section 33, at least in the vicinity of transition 32, will be no more than about 0.005 inches and preferably no more than about 0.003 inches to provide an effective seal in a blood environment. A larger clearance may be more feasible in Following positioning of the distal end of proximal section 33 within the vasculature, such as within the cervical carotid artery, the control 24 is manipulated to distally advance distal section 34 deeper into the vasculature. For this purpose, the pull wire 42 will be provided with sufficient column strength to enable distal advance of the distal tip 38 as will be discussed below.

The pull wire 42 and distal section 34 may be integrated into a catheter as illustrated in FIGS. 1 and 2. Alternatively, distal section 34 and pull wire 42 may be configured as a stand-alone catheter extension device as is discussed in greater detail below. The catheter extension device may be introduced into the proximal end of proximal section 33 after placement of proximal section 33 and advanced distally there through as illustrated in FIG. 3A, to telescopically extend the reach of the aspiration system.

Referring to FIG. 3B, the pull wire 42 may comprise a tubular wall having an axially extending central lumen 45. The central lumen 45 permits introduction of media such as lubricants, drugs, contrast agents or others into the distal section 34. In addition, the central lumen 45 extending through pull wire 42 permits introduction of an agitator as is discussed in greater detail below. As shown in FIG. 3B, the central lumen 45 may open into the lumen 40. The distal opening of the central lumen 45 may be positioned at a point along the length of the distal section 34 such that the central lumen 45 terminates where the lumen 40 begins (the distal opening of central lumen 45 may be longitudinally aligned with the proximal opening of lumen 40). The proximal opening of lumen 40 may be angled or slanted as shown in FIG. 3B. In some embodiments, the opening of lumen 40 may be flat. The distal opening of central lumen 45 may be flat as shown in FIG. 3B. In some embodiments, the opening may be angled or slanted, similar to the opening of lumen 40 in FIG. 3B.

In some embodiments, the central lumen 45 may terminate proximal to the opening of the lumen 40. In some embodiments, the central lumen 45 may terminate distal to the opening of the lumen 40 and/or the proximal end of the distal section 34 (e.g., at a point within the lumen 40). For example, the central lumen 45 may terminate at the distal end of the distal section or just short of the distal end (e.g., no more than approximately 1 cm from the distal end). In some implementations, the portion of the pull wire 42, with or without a central lumen 45, which extends beyond the proximal end of the distal section 34 (e.g., into lumen 40) may decrease in stiffness (durometer) in a distal direction. The pull wire 42 may be relatively stiff along the portion proximal to the proximal end of the distal section 34 in order to provide sufficient pushability of the extension catheter. The stiffness of the portion of the pull wire 42 distal of the proximal end of the distal section 34 may substantially match or be less than the stiffness of the distal section 34 along the length of the distal section 34. The portion of the pull wire 42 distal of the proximal end of the distal section 34 may have a uniform stiffness less than the stiffness of the portion proximal of the proximal end of the distal section 34 or it may have a gradated or gradually decreasing stiffness in the distal direction, decreasing from the stiffness of the portion proximal of the proximal end of the distal section 34. For example, the pull wire 42 may comprise metal along the portion proximal to the proximal end of the distal section 34 and may comprise a polymer, softer than the metal, along the portion distal to the proximal end of the distal section 34. The portion distal to the proximal end, in some embodiments, may be extruded with decreasing stiffness in the distal direction.

The proximal end 12 of catheter 10 may be additionally provided with a manifold 18 having one or more access ports as is known in the art. Generally, manifold 18 is provided with a proximal port such as a guidewire port 20 in an over-the-wire construction, and at least one side port such as aspiration port 22. Alternatively, the aspiration port 22 may be omitted if the procedure involves removal of the guidewire proximally from the guidewire port 20 following placement of the aspiration catheter, and aspiration through the guidewire port. Additional access ports and lumen may be provided as needed, depending upon the functional capabilities of the catheter. Manifold 18 may be injection molded from any of a variety of medical grade plastics, or formed in accordance with other techniques known in the art.

Manifold 18 may additionally be provided with a control 24, for controlling the axial position of the distal segment 34 of the catheter. Control 24 may take any of a variety of forms depending upon the mechanical structure and desired axial range of travel of the distal segment 34. In the illustrated embodiment, control 24 comprises a slider switch which is mechanically axially movably linked to the distal segment such that proximal retraction of the slider switch 24 produces a proximal movement of the distal segment 34. This retracts the distal segment 34 into the proximal section 33 as illustrated in FIG. 1. Distal axial advancement of the slider switch 24 produces a distal axial advance of the distal segment 34, as illustrated in FIGS. 2 and 3.

Any of a variety of controls may be utilized, including switches, buttons, levers, rotatable knobs, pull/push wires, and others which will be apparent to those of skill in the art in view of the disclosure herein. The control will generally be linked to the distal segment by a control wire 42.

Alternatively, the proximal section 33 and distal section 34 maybe provided as separate devices, in which construction the proximal control may be omitted. The distal end of proximal section 33 may be provided with one or more jaws for morcellating or otherwise breaking thrombus or other obstruction into pieces or otherwise facilitating aspiration. The proximal section 33 may additionally be mechanically coupled to or adapted for coupling to a source of vibrational or rotational movement, such as to provide the intermittent or pulsatile movement to facilitate navigation into the vasculature.

Using axial reciprocation, and/or rotation, and/or biting action of the distal jaws, the clinician may be able to reach the obstruction using proximal section 33. See, for example, FIG. 4 in which proximal section 33 is able to reach an obstruction in the left carotid siphon. If, however, the proximal section 33 is not able to advance sufficiently close to the obstruction, a separate telescoping distal section 34 may be introduced into the proximal section 33 and advanced therethrough and beyond, as illustrated in FIGS. 2 and 5-9, to reach the obstruction.

The cerebral circulation is regulated in such a way that a constant total cerebral blood flow (CBF) is generally maintained under varying conditions. For example, a reduction in flow to one part of the brain, such as in acute ischemic stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

FIG. 4 depicts cerebral arterial vasculature including the Circle of Willis. Aorta 100 gives rise to right brachiocephalic artery 82, left common carotid artery (CCA) 80, and left subclavian artery 84. The brachiocephalic artery 82 further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

When an occlusion occurs acutely, for example, in left carotid siphon 70, as depicted in FIG. 4, blood flow in the right cerebral arteries, left external carotid artery 78, right vertebral artery 76 and left vertebral artery 77 increases, resulting in directional change of flow through the Circle of Willis to compensate for the sudden decrease of blood flow in the left carotid siphon. Specifically, blood flow reverses in right posterior communicating artery 72, right PCA 74, left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal the occlusion to provide perfusion to the ischemic area distal to the occlusion.

As illustrated in FIG. 4, the proximal segment of catheter 10 is transluminally navigated along or over the guidewire, to the proximal side of the occlusion. Transluminal navigation may be accomplished with the distal section 34 of the catheter in the first, proximally retracted configuration. This enables distal advance of the proximal section 33 until further progress is inhibited by small and/or tortuous vasculature. Alternatively, the distal section 34 is a separate device, and is not inserted into the proximal section 33 until it is determined that the proximal section 33 cannot safely reach the occlusion. In the example illustrated in FIG. 4, the occlusion may be safely reached by the proximal section 33, without the need to insert or distally extend a distal section 34.

The distal end of the proximal section 33 of aspiration catheter 10 is inserted typically through an incision on a peripheral artery over a guidewire and advanced as far as deemed safe into a more distal carotid or intracranial artery, such as the cervical carotid, terminal ICA, carotid siphon, MCA, or ACA. The occlusion site can be localized with cerebral angiogram or IVUS. In emergency situations, the catheter can be inserted directly into the symptomatic carotid artery after localization of the occlusion with the assistance of IVUS or standard carotid doppler and TCD.

If it does not appear that sufficient distal navigation of the proximal section 33 to reach the occlusion can be safely accomplished, the distal section 34 is inserted into the proximal port 20 and/or distally extended beyond proximal section 33 until distal tip 38 is positioned in the vicinity of the proximal edge of the obstruction.

Figure 5:
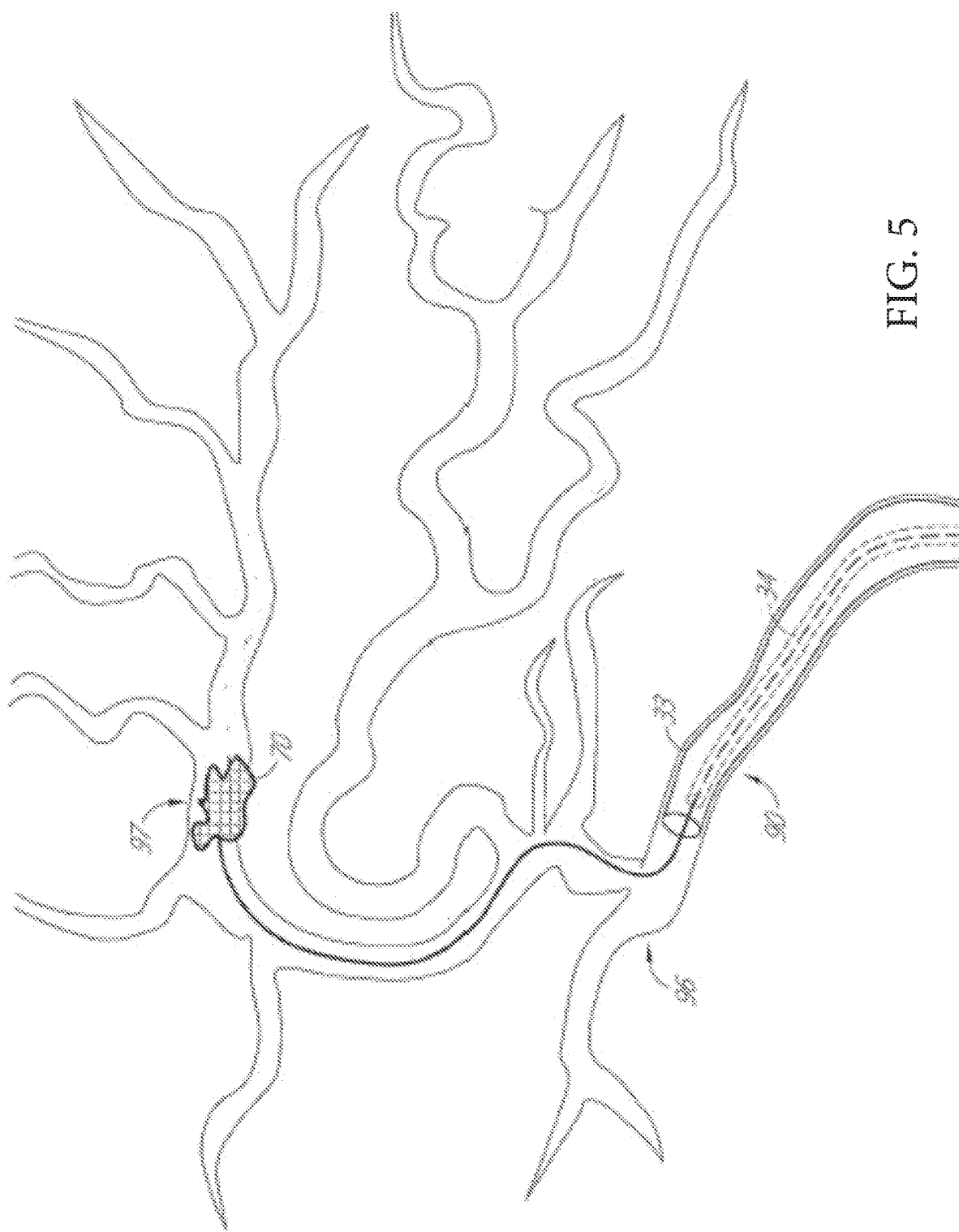
FIGS. 5 through 8 show a sequence of steps involved in positioning of the catheter and aspirating obstructive material from the middle cerebral artery.
Figure 6:
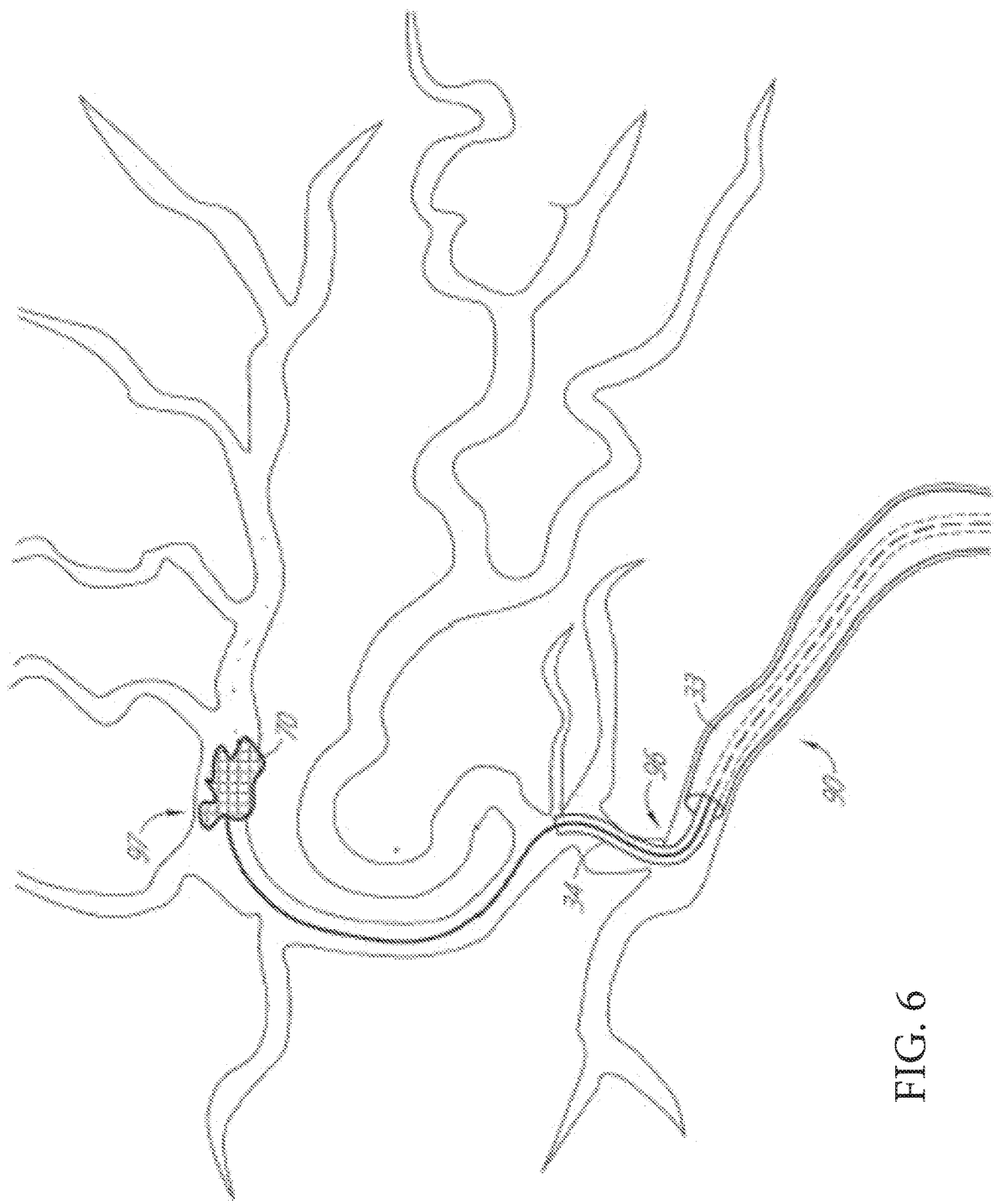
Figure 7:
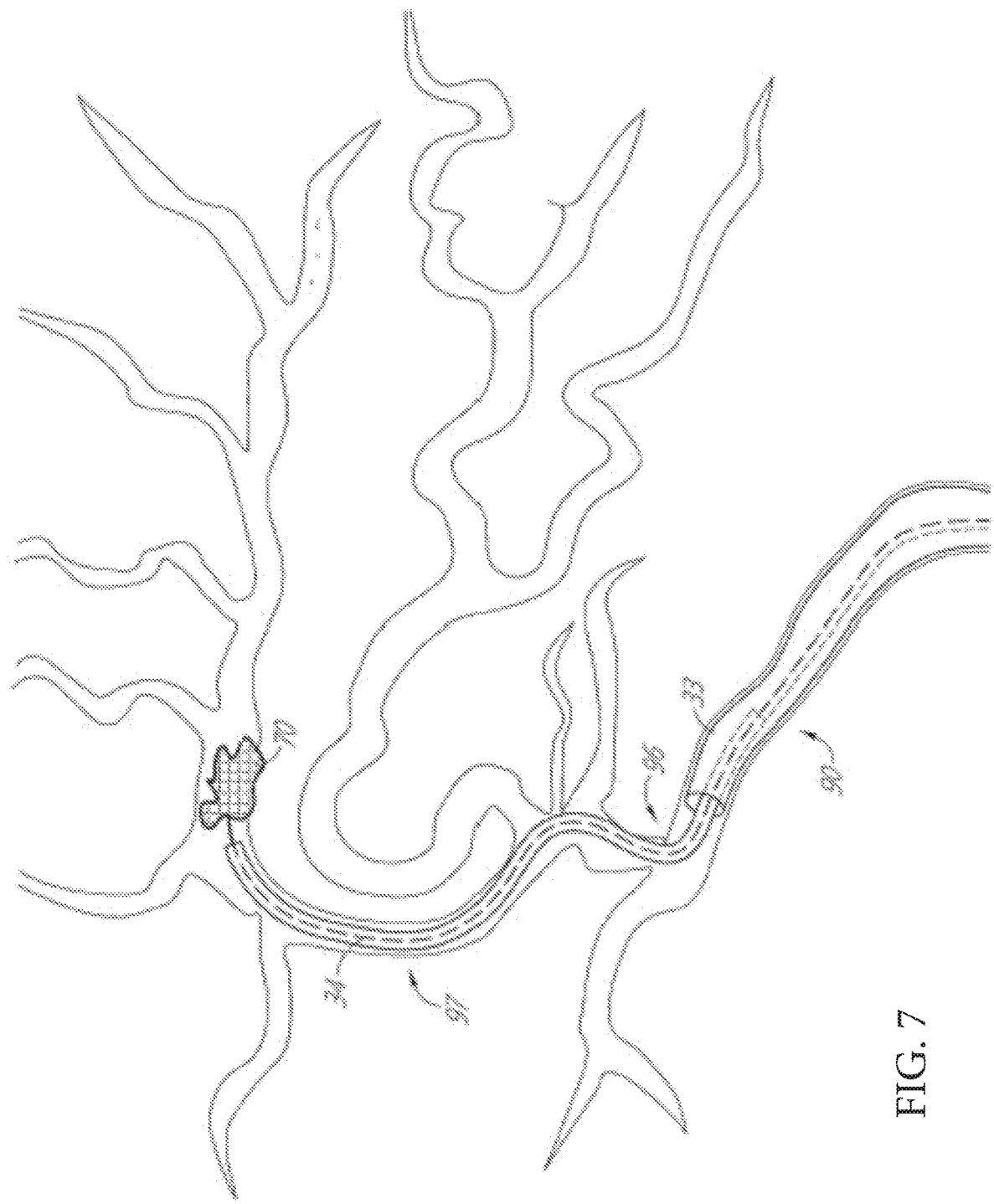

Referring to FIG. 5, an obstruction 70 is lodged in the middle cerebral artery 97. Proximal section 33 is positioned in the ICA and not able to navigate beyond a certain point such as at the branch 96 to the MCA artery 97. The proximal section 33 may be provided with a distal section 34 carried there in. Alternatively, a separate distal section 34 may be introduced into the proximal end of proximal section 33 once the determination has been made that the obstruction 70 cannot be reached directly by proximal section 33 alone. As seen in FIGS. 6 and 7, the distal section 34 may thereafter be transluminally navigated through the distal tortuous vasculature between proximal section 33 and the obstruction 70.

Figure 8:
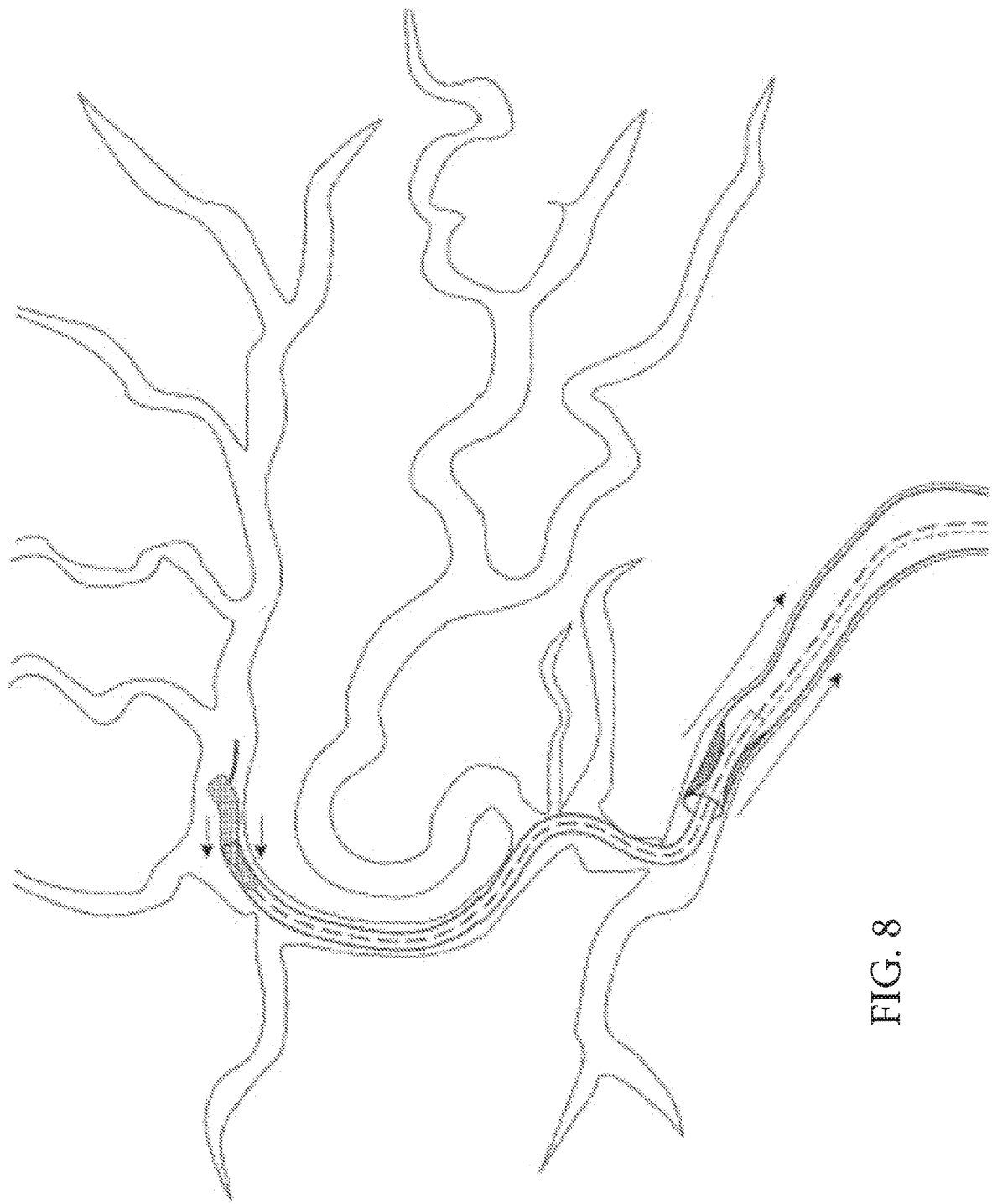
Figure 9:
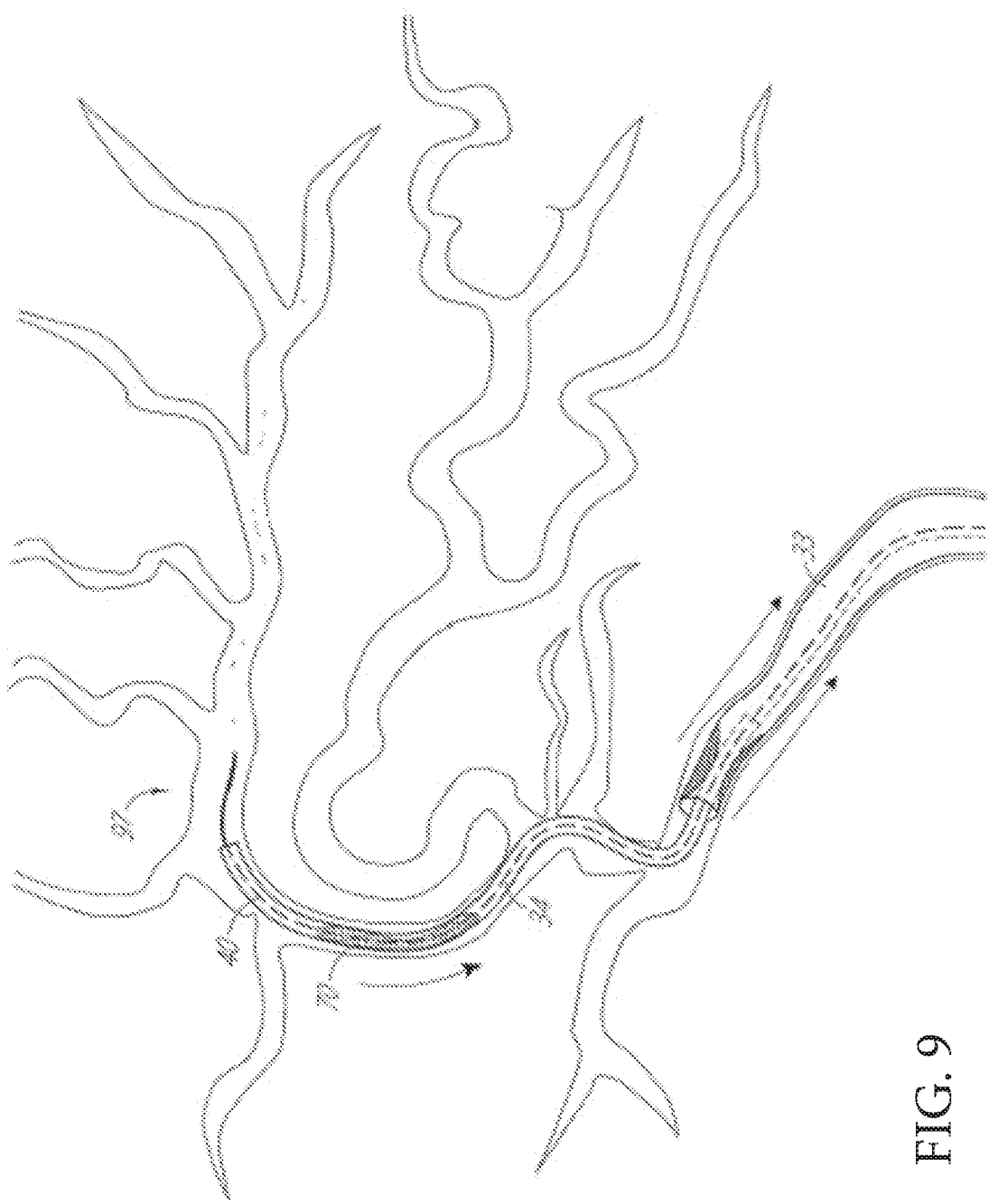
FIG. 9 illustrates removal of the catheter following aspiration of obstructive material.

Referring to FIG. 8, the obstruction 70 may thereafter be drawn into distal section 34 upon application of constant or pulsatile negative pressure with or without the use of jaws or other activation on the distal end of distal section 34 as discussed elsewhere herein. Once the obstruction 70 has either been drawn into distal section 34, or drawn sufficiently into distal section 34 that it may be proximately withdrawn from the body, proximal section 33 and distal section 34 are thereafter proximally withdrawn.

Aspiration may be applied via lumen 40, either in a constant mode, or in a pulsatile mode. Preferably, pulsatile application of vacuum will cause the distal tip 38 to open and close like a jaw, which facilitates reshaping the thrombus or biting or nibbling the thrombus material into strands or pieces to facilitate proximal withdrawal under negative pressure through lumen 40. Application of aspiration may be accompanied by distal advance of the distal tip 38 into the thrombotic material.

Pulsatile application of a vacuum may oscillate between positive vacuum and zero vacuum, or between a first lower negative pressure and a second higher negative pressure. Alternatively, a slight positive pressure may be alternated with a negative pressure, with the application of negative pressure dominating to provide a net aspiration through the lumen 40. Pulse cycling is discussed in greater detail elsewhere herein.

The proximal manifold and/or a proximal control unit (not illustrated) connected to the manifold may enable the clinician to adjust any of a variety o/f pulse parameters including pulse rate, pulse duration, timing between pulses as well as the intensity of the pulsatile vacuum.

The distal section may thereafter be proximally retracted into proximal section 33 and the catheter proximally retracted from the patient. Alternatively, proximal retraction of the catheter 10 may be accomplished with the distal section 34 in the distally extended position. A vasodilator, e.g., nifedipine or nitroprusside, may be injected through a second lumen to inhibit vascular spasm induced as a result of instrumentation.

Pressure may be monitored by a manometer carried by the catheter or a wire positioned in a lumen of the catheter. A pressure control and display may be included in the proximal control unit or proximal end of the catheter, allowing suction within the vessel to be regulated.

Focal hypothermia, which has been shown to be neuroprotective, can be administered by perfusing hypothermic oxygenated blood or fluid. Moderate hypothermia, at approximately 32 to 34° C., can be introduced during the fluid infusion. Perfusion through a port on manifold 18 can be achieved by withdrawing venous blood from a peripheral vein and processing through a pump oxygenator, or by withdrawing oxygenated blood from a peripheral artery, such as a femoral artery, and pumping it back into the carotid artery.

If continuous and/or intermittent suction fails to dislodge the occlusion, a thrombolytic agent, e.g., t-PA, can be infused through central lumen 40 or a second lumen to lyse any thrombotic material with greater local efficacy and fewer systemic complications. Administration of thrombolytic agent, however, may not be recommended for devices which are inserted directly into the carotid artery due to increased risk of hemorrhage.

The intensity of intermittent or pulsatile vacuum applied to lumen 40 may be adjusted to cause the distal tip 38 of the catheter 10 to experience an axial reciprocation or water hammer effect, which can further facilitate both translumenal navigation as well as dislodging or breaking up the obstruction. Water hammer, or more generally fluid hammer, is a pressure surge or wave caused when a fluid in motion is forced to stop or change direction suddenly, creating a momentum change. A water hammer commonly occurs when a valve closes suddenly at the end of a pipeline system, and a pressure wave propagates in the pipe. A pressure surge or wave is generated inside the lumen 40 of the aspiration catheter 10 when a solenoid or valve closes and stops the fluid flow suddenly, or other pulse generator is activated. As the pressure wave propagates in the catheter 10, it causes the catheter 10 to axially vibrate. Since vibration can reduce surface friction between the outer diameter of the catheter 10 and the inner diameter of the vessel wall, it enables catheter to track through tortuous anatomies as well as assist capturing thrombus.

Figure 10:
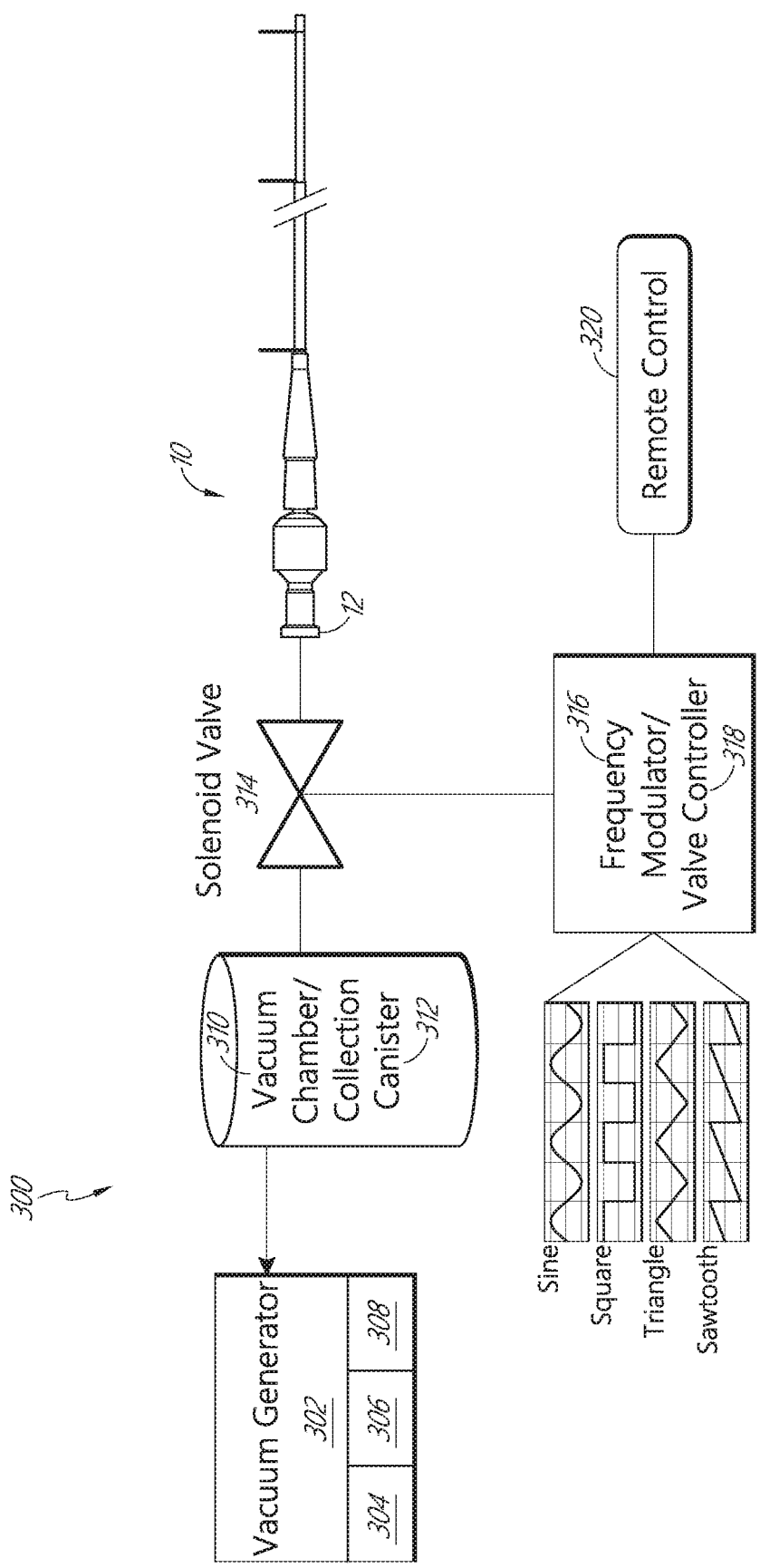
FIG. 10 illustrates an aspiration system configured to apply pulsatile negative pressure through the aspiration catheter.

A pulsatile vacuum pressure aspirator may be used in order to improve effectiveness of aspiration for vascular thrombectomy and to improve catheter trackability through tortuous vasculatures. FIG. 10 shows an embodiment of a pulsatile vacuum pressure aspirator 300 that applies intermittent or pulsatile vacuum to lumen 40. In the illustrated embodiment, the pulsatile vacuum pressure aspirator 300 is in fluid connection with the proximal end 12 of the catheter 10 and comprises vacuum generator 302, vacuum chamber 310, collection canister 312, solenoid valve 314, frequency modulator 316, valve controller 318, and remote controller 320.

Vacuum generator 302 comprises a vacuum pump 304, a vacuum gauge 306, and a pressure adjustment control 308. The vacuum pump 304 generates vacuum. The vacuum gauge 306 is in fluid connection with the vacuum pump 304 and indicates the vacuum pressure generated by the pump 304. The pressure adjustment control 308 allows the user to set to a specific vacuum pressure. Any of a variety of controls may be utilized, including switches, buttons, levers, rotatable knobs, and others which will be apparent to those of skill in the art in view of the disclosure herein.

Vacuum chamber 310 is in fluid connection with the vacuum generator 302 and acts as a pressure reservoir and/or damper. Collection canister 312 is in fluid connection with the vacuum chamber 310 and collects debris. The collection canister 312 may be a removable vial that collects debris or tissues, which may be used for pathologic diagnosis. Vacuum chamber 310 and collection canister 312 may be separate components that are in fluid connection with each other or a merged component. In the illustrated embodiment, the vacuum chamber 310 and the collection canister 312 is a merged component and is in fluid connection with the vacuum generator 302.

Solenoid valve 314 is located in the fluid connection path between a luer or other connector configured to releasably connect to an access port of the catheter 10 and the vacuum chamber 310/collection canister 312. The solenoid valve 314 controls the fluid flow from the catheter 10 to the vacuum chamber 310/collection canister 312.

Pulsatile vacuum pressure aspirator 300 may comprise frequency modulator 316 for control of the solenoid valve 314. The frequency modulator 316 generates different electrical wave frequencies and forms, which are translated into the movement of the solenoid valve 314 by the valve controller 318. The wave forms generated from the frequency modulator 316 comprise sinusoidal, square, and sawtooth waves. The wave forms generated from the frequency modulator 316 typically have frequencies less than about 500 Hz, in some modes of operation less than about 20 Hz or less than about 5 Hz. The wave forms have duty cycles ranging from 0%, in which the solenoid valve 314 is fully shut, to 100%, in which the solenoid valve 314 is fully open.

Valve controller 318 modulates the solenoid valve 314 on and off. The valve controller 318 may be electrically or mechanically connected to the solenoid valve 314. Any of a variety of controls may be utilized, including electrical controllers, switches, buttons, levers, rotatable knobs, and others which will be apparent to those of skill in the art in view of the disclosure herein. The valve controller 318 may be mechanically controlled by users or may be electrically controlled by the frequency modulator 316. The frequency modulator 316 and the valve controller 318 may be separate components that are electrically or mechanically connected or a merged component.

Remote control 320 enables physicians to control the frequency modulator 316 and/or the valve controller 318 for various purposes, such as turning the valve on/off, selecting different wave frequencies, and selecting different wave forms, while manipulating the catheter 10 at the patient side. Remote control 320 may be in wired or wireless communication with aspirator 300.

By tuning frequency, duty cycle, and wave form, one skilled in the art may match or approximate the resonating frequency to the natural frequency of the catheter. This may further enhance the efficacy of aspiration. The natural frequency of the catheter is typically less than about 260 Hz.

Figure 11:
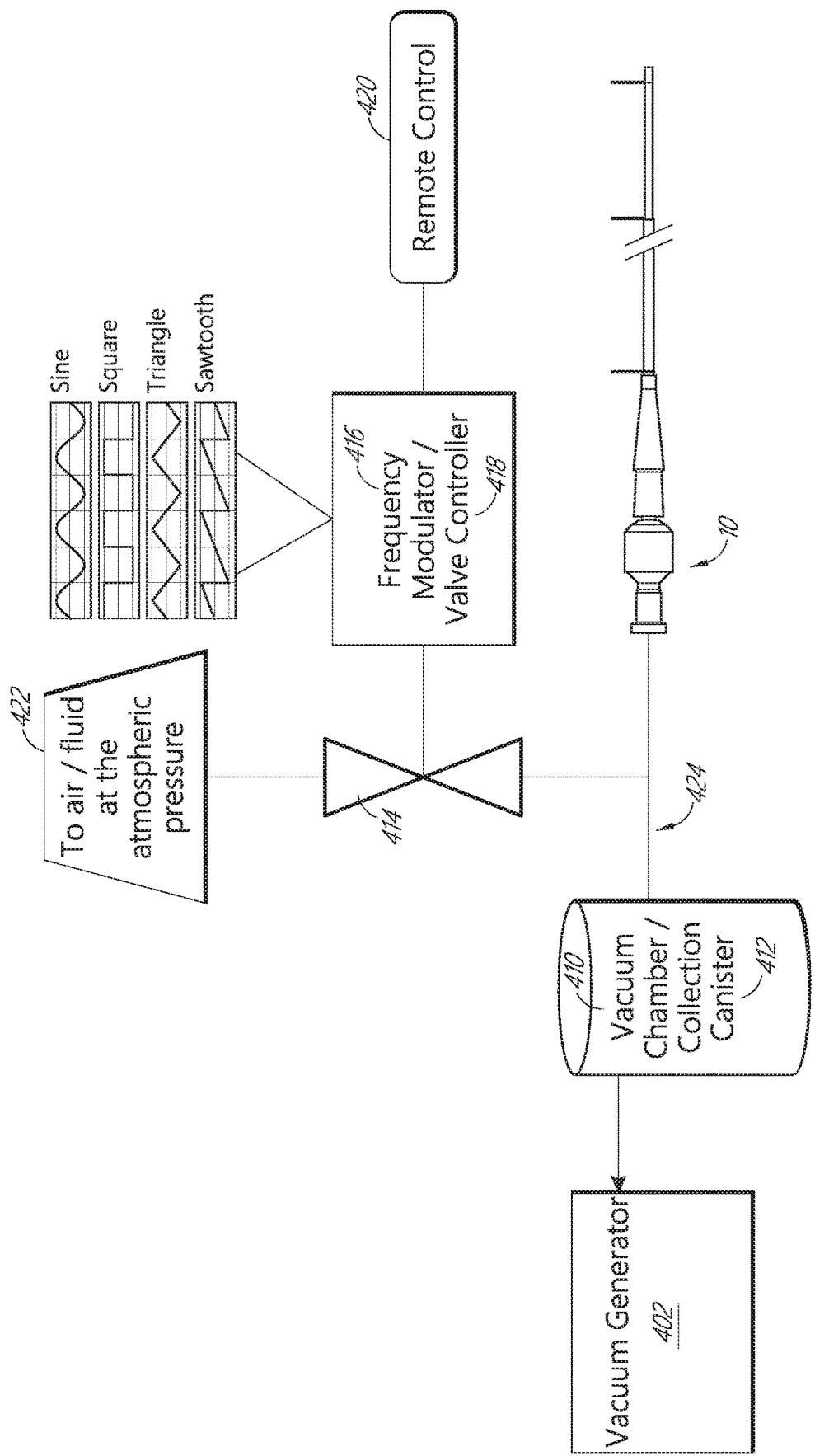
FIG. 11 illustrates an alternative aspiration system configured to apply pulsatile negative pressure through the aspiration catheter.

In another embodiment, shown in FIG. 11, the solenoid valve 414 is positioned in and fluidly connects between the air/fluid reservoir 422 at the atmospheric pressure and the aspiration line 424 connecting the catheter 10 to the vacuum chamber 410/collection canister 412. Unlike the first embodiment in FIG. 10, this system modulates pressure in the catheter 10 by allowing pressure to vary from vacuum to atmospheric pressure. When the solenoid valve 414 is open to the air/fluid reservoir 422 at the atmospheric pressure, the vacuum pressure in the aspiration line 424 decreases to the atmospheric pressure. When the solenoid valve 414 is closed, it increases the vacuum pressure in the aspiration line 424.

Figure 12:
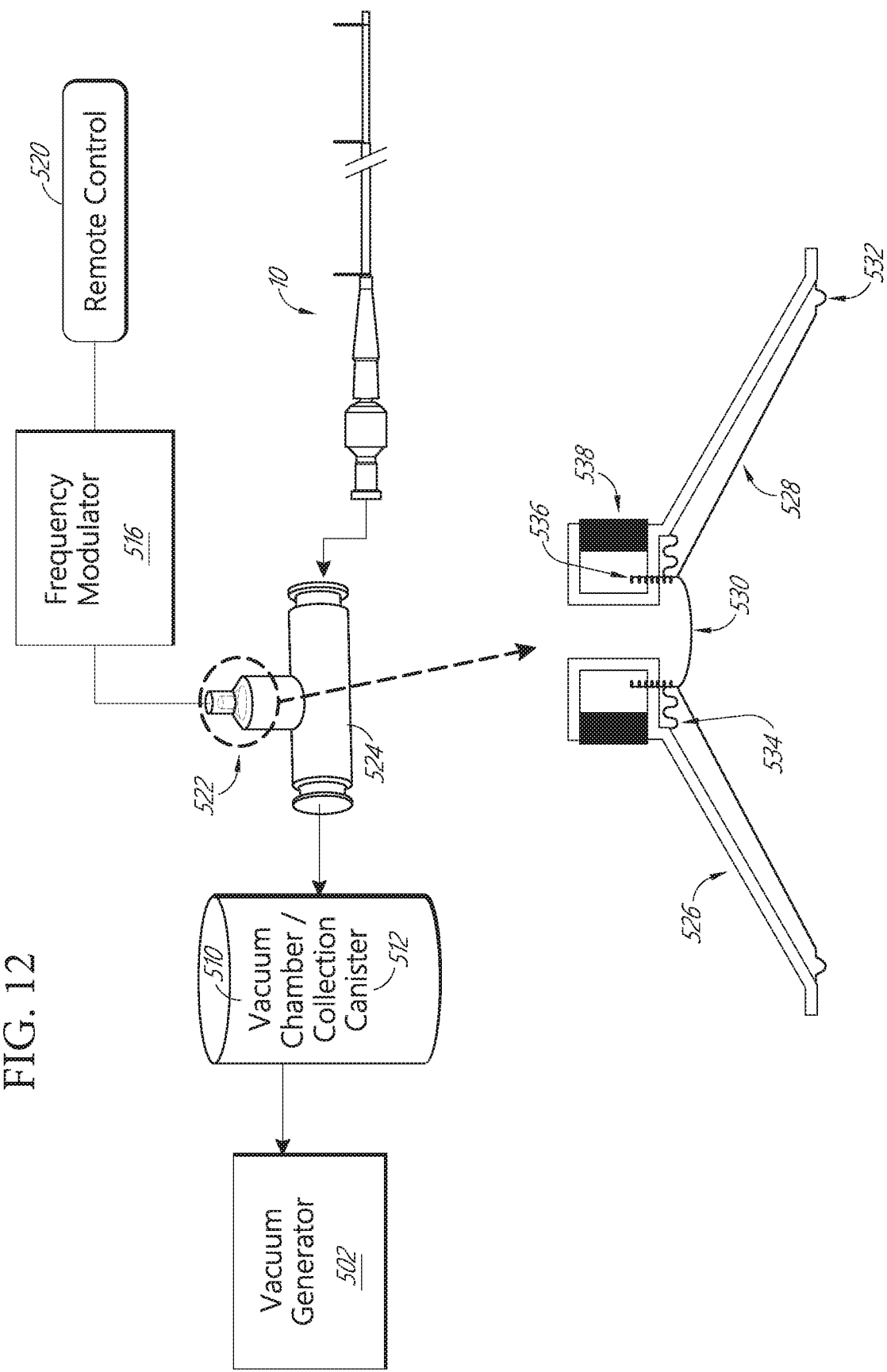
FIG. 12 illustrates a further alternative aspiration system configured to apply mechanical vibration through the aspiration catheter.

In yet another embodiment, shown in FIG. 12, an electromagnetic actuated diaphragm 522 is attached to the aspiration line 524 connecting the catheter 10 to the vacuum chamber 510/collection canister 512. The electromagnetic actuated diaphragm 522, which is similar to that of a speaker driver, generates acoustic pressure waves in the catheter 10. The diaphragm 522 typically has a structure similar to a speaker driver and comprises frame 526, cone 528, dust cap 530, surround 532, spider or damper 534, voice coil 536 and magnet 538. Strength of the acoustic pressure waves may be modulated by the strength of the magnet 538. The frequency modulator 516 connected to the remote control 520 is electrically connected to the diaphragm 522 and generates different electrical wave frequencies and forms, which are translated by the diaphragm 522 into acoustic pressure waves in the aspiration line 524 and the catheter 10.

Media may be infused into/around the clot area to help liberate the clot from the vasculature.

Figure 13A:
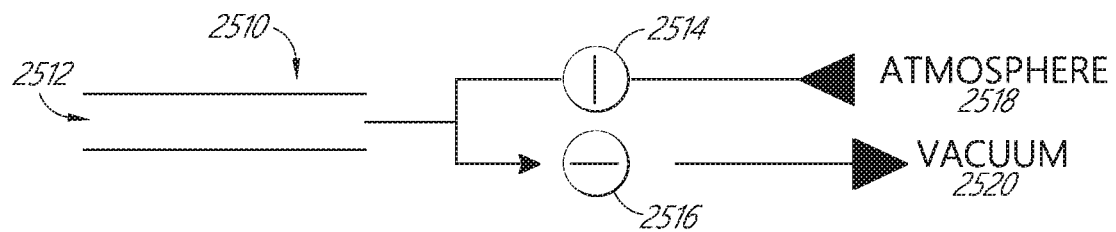
FIGS. 13A-13C depict a pulsed aspiration cycle according to an embodiment.
Figure 13B:
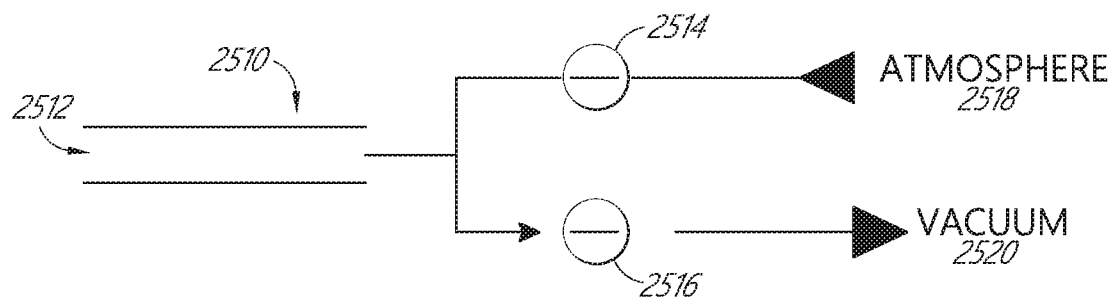
Figure 13C:
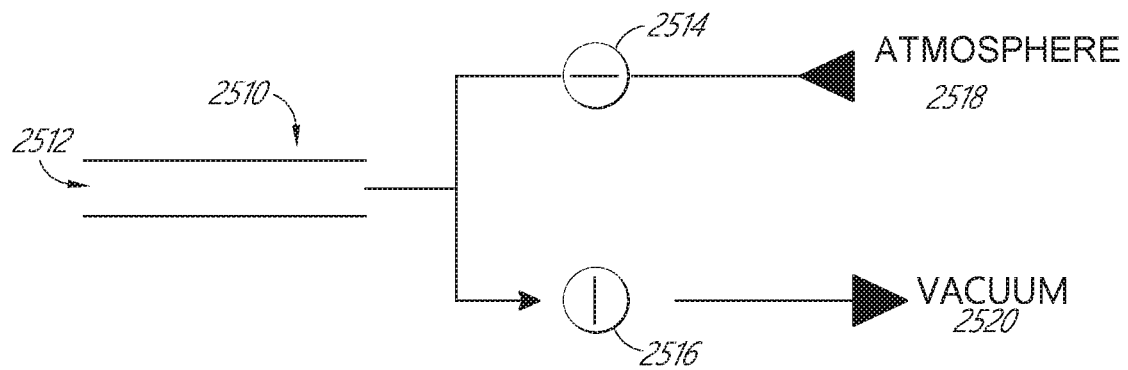

Referring to FIGS. 13A-13C, experiments showed that an interrupted vacuum can help aspirating a corked clot stuck at the distal end 2512 of the catheter 2510 by loosening the clot and reshaping it to fit into the catheter 2510 after each vacuum and release cycle. Merely stopping the vacuum is not sufficient to loosen the clot. Completely releasing (venting to atmospheric pressure) the vacuum and allowing the clot to relax before reapplying a vacuum is found to aspirate the corked clot most efficiently. The period of each vacuum and release cycle may be equal to or greater than about 0.1, 0.5, 1, 2, 3, 4, 5, 6, 7, 8, 9, or 10 seconds.

FIGS. 13A-13C show a logical progression of the vacuum and release cycle as applied to the catheter 2510. A release line 2518 and a vacuum line 2520 are connected to or near the proximal end of the catheter 2510. The release line 2518 is in communication with atmospheric pressure on its proximal end and has a release valve 2514 configured to open or close the fluid communication between the catheter 2510 and the vacuum. The vacuum line 2520 is connected to vacuum on its proximal end and has a vacuum valve 2516 configured to open or close the fluid communication between the catheter 2510 and the vacuum.

In the first step as shown in FIG. 13A, the release valve 2514 is closed, and the vacuum valve 2516 is open such that the vacuum is applied to the catheter 2510 to aspirate the clot. Then, as shown in FIG. 13B, the release valve 2514 is opened while the vacuum valve 2516 stays open. Because the release line 2518 and the vacuum line 2520 are in fluid communication, either directly or via at least a portion of the catheter 2510, the vacuum is applied mainly through the release line 2518, dropping vacuum applied to the catheter. Finally, as shown in FIG. 13C, the vacuum valve 2516 is shut off, allowing the vacuum to be completely released and the clot to relax. Then, another cycle from FIG. 13A to FIG. 13C begins by closing the release valve 2514 and opening the vacuum valve 2516.

The method of retrieving a clot may comprise providing the aspiration catheter, an agitator longitudinally extending or positionable inside the lumen of the aspiration catheter, and a driver coupled to the proximal end of the agitator; placing the catheter adjacent to the clot; attempting to aspirate clot; if not successful, advancing an agitator distally through the catheter; activating the driver to rotate the agitator and loosen the clot; optionally injecting media through the agitator to lubricate the clot and/or create a media jet from the distal end of the agitator, configured to help aspirate the clot; transporting the clot proximally inside the lumen of the catheter by applying the vacuum at the proximal end of the catheter; and optionally pulsing the vacuum. As pieces of the clot separate, transport may be assisted by the rotating agitator and/or injection media.

In order to detach a more stubborn clot, aspiration, media injection, and/or rotation of the wire or hypo tube may be timed. Building up a surplus of media around the clot will form a plug. When aspiration is activated and/or pulsed, the vacuum can draw the "plug" proximally inside the lumen of the wire or hypo tube like a syringe plunger. A higher local vacuum around the clot is maintained, and more momentum is added to the "plug" as more media is added. Timing the rotation of the wire or hypo tube with aspiration and media injection may help wiggle or fatigue the clot and detach it out of the vasculature.

The catheter 10 may comprise a manifold at its proximal end, as described elsewhere herein. In some embodiments, a manifold 18 may configured to be coupled to the proximal section 33 of the tubular body 16 of catheter 10. The manifold 18 may be removably attachable to the proximal section 33 or the manifold, or at least a portion thereof, may be permanently attached to the proximal section 33. The distal section 34 may be axially translatable through the proximal section 33, as described elsewhere herein, such that the total length of the catheter 10 may be extendable by the distal section 34, as shown in FIG. 2. The distal section 34 may have a smaller diameter and cross-sectional area than the proximal section 33 to allow the distal section 34 to be received within the lumen of the proximal section 33. In some embodiments, the distal section 34 may be axially translatable through the manifold 18 and may removable from the proximal section 33 by retracting the distal section 34 through a proximal end of the manifold 18.

In some implementations, the distal section 34 may be extended through the proximal section 33 and the clot may be aspirated through or captured on the distal end 38 of the distal section 34. In situations in which the clot is not aspirated into the lumen 40 of the distal section 34 (e.g., the clot is too large to fully enter the lumen 40), the clot may be retained, at least to a degree, on the distal end 38 via the suction force of aspiration through the distal section 34. In many circumstances, the clot may be subsequently removable via aspiration through the larger diameter proximal section 33. The distal section 34 may be proximally retracted through the proximal section 33 such that the distal end 38 of the distal section 34 is retracted proximally past the distal end of the proximal section 33. At such a point the clot may either be drawn into the lumen of the proximal section 33 or the clot may become captured on the distal end of the proximal section 33 via the suction force extending through the proximal section 33 of the catheter 10. In scenarios in which the clot is ingested into the lumen of the proximal section 33, the clot is likely to remain stuck on the distal end 14 of the distal section 33. The distal section 33 may be proximally withdrawn from the catheter 10 bringing the clot with it. In embodiments, in which separate aspiration lines are provided to the proximal section 33 and the distal section 34, whether connected to the same or different vacuum sources, the clot may become dislodged from the distal end 38 of the distal section 34 and aspirated through the aspiration line connected to the proximal section 33 as the distal end 38 of the distal section 34 approaches or passes the aspiration line to the proximal section 33. Otherwise, the clot may be removed through the proximal end of the proximal section 33 or manifold with the distal section 34 as it is withdrawn. In scenarios in which the clot is stuck on the distal end of the proximal section 33 or becomes stuck within the lumen of the proximal section 33, it may be advantageous to remove the distal section 34 from the lumen of the proximal section 33 to increase the effective cross-sectional area of the proximal section 33. To do so, it may be necessary, in some embodiments, to remove the distal section 34 entirely from the manifold at the proximal end of the proximal section 33.

In some embodiments, it may be necessary to open, at least partially, or to increase an opening in a proximal valve of a manifold to remove the distal section 34 from the manifold. For instance, in embodiments where the distal section 34 is coupled at its proximal end to a pull wire 42, the pull wire 42 may extend through a proximal valve or port of the manifold. The proximal valve or port may be closed, at least partially, around the pull wire 42, allowing a user to manually retract or extend the distal section 34 by manipulating the portion of the pull wire 42 extending proximally from the manifold. In order, to proximally, withdraw the entire distal section 34 from the manifold, the proximal valve or port would need to be further opened to allow the tubular body 16 of the distal section 34, which comprises a larger outer diameter than the pull wire 42, to be removed from the manifold 18. In some embodiments, further opening the proximal valve or port may cause a loss or substantial decrease in the vacuum pressure applied to the catheter 10, as the lumen 40 of the distal section will be placed in fluid communication with the ambient atmosphere when the proximal port or valve is opened to allow the distal section 34 to pass through. Additionally or alternatively, vacuum pressure may be lost through the proximal port or valve opening in the space around the distal section 34 as it is withdrawn. This valve or port may not be maximally tightened or closed in order to allow movement of the distal section 34 through the valve or port. This loss in vacuum pressure, even if only transient, may cause the release of clots stuck on the end of the proximal section 33, may cause release of clots stuck on the end of the distal section 34, and/or may cause clots trapped within the lumens of either the proximal section 33 or distal section 34 to flow distally out of the respective lumen.

Figure 14A:
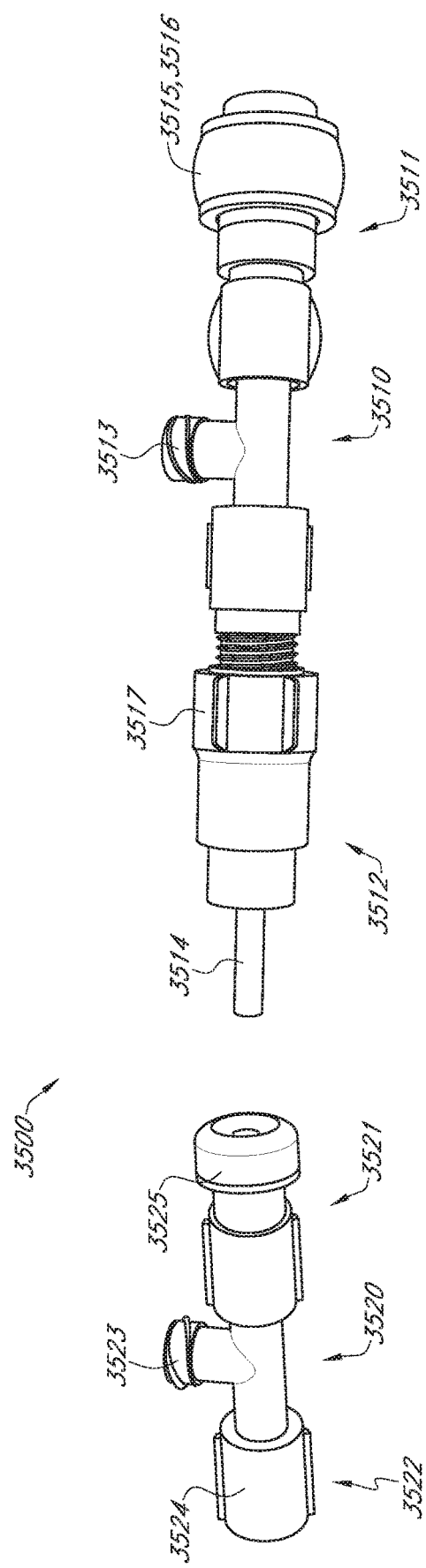
FIGS. 14A-14C illustrate perspective views of an example of a vacuum transfer device.
Figure 14B:
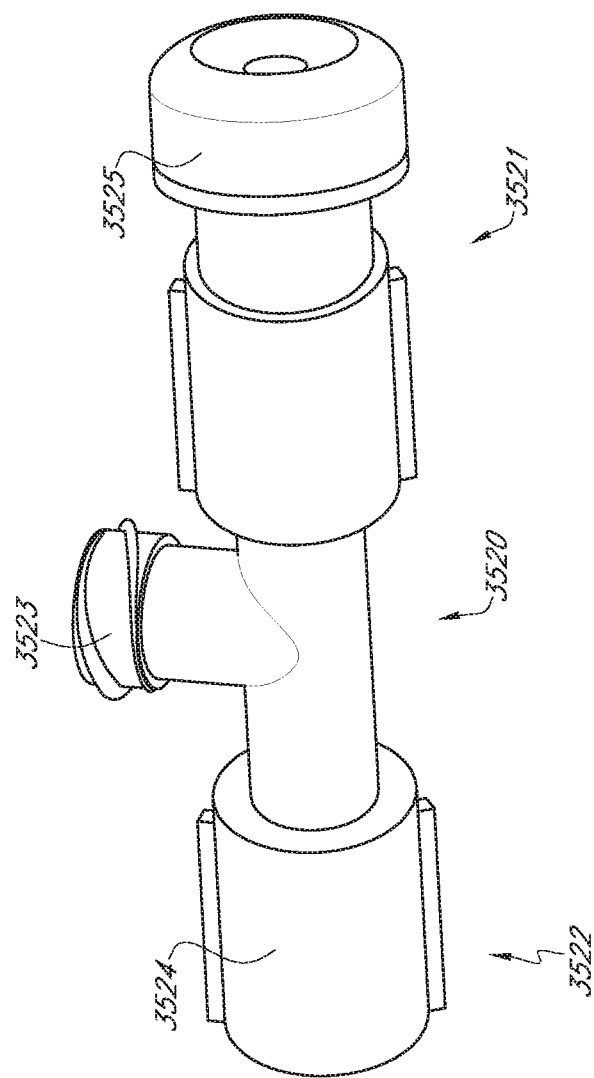
Figure 14C:
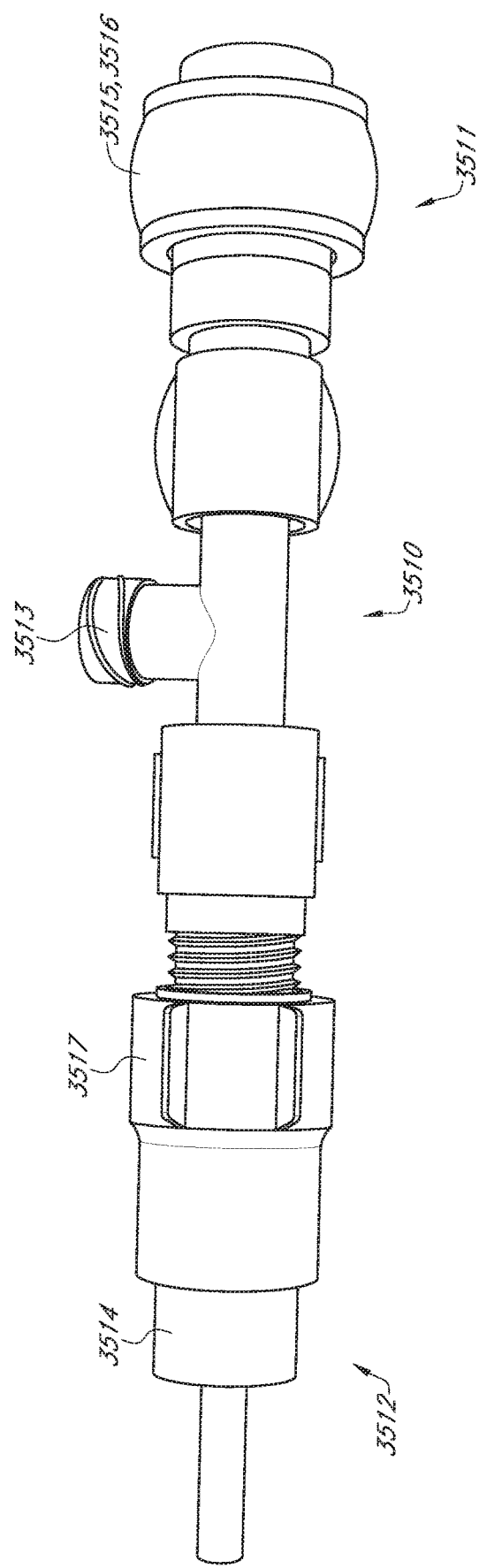

In some embodiments, the loss of vacuum pressure at the distal ends of the proximal section 33 and distal section 34 may be prevented via a vacuum transfer tool 3500. The vacuum transfer tool 3500 may effectively "transfer" vacuum to the proximal section 33 as the distal section is withdrawn from the proximal section 33. FIG. 14A depicts an example of a vacuum transfer tool 3500. The vacuum transfer tool 3500 may replace or function as the manifold 18 or may be coupled to the proximal end of the manifold 18 or another manifold coupled to the proximal end of the proximal section 33 of the catheter 10. The vacuum transfer tool 3500 can maintain vacuum pressure on the proximal section 33 of the catheter 10 independently of the distal section 34 of the catheter 10, allowing removal of the distal section 34 from the proximal section 33 without a loss or drop in vacuum pressure. The transfer tool 3500 may comprise a proximal transfer tube 3510 and a distal transfer tube 3520, the proximal transfer tube 3510 being configured to be positioned proximal to the distal transfer tube 3520. FIG. 14B shows a close-up of the distal transfer tube 3520 and FIG. 14C shows a close-up of the proximal transfer tube 3510. The distal transfer tube 3520 may have a proximal end 3521 and a distal end 3522 and a central lumen extending along a longitudinal axis from the proximal end 3521 to the distal end 3522. The central lumen of the distal transfer tube may comprise a minimum diameter configured to receive the proximal section 33, or at least an introducer (described elsewhere herein), or at least the distal section 34 of the catheter 10, such that the distal section 34 may be readily axially translated (e.g., slid) through the central lumen. The distal end 3522 of the distal transfer tube 3520 may be coupled to proximal end of the proximal section 33 of catheter 10 or the proximal end of the manifold 18 (or another manifold) forming a fluid tight seal between the two. The distal transfer tube 3520 may be permanently coupled to the proximal section 33 or manifold or it may be removably attachable to the proximal section 33 or manifold. In some embodiments, a portion of the proximal section 33 or of the manifold may be received within the distal transfer tube 3520.

The proximal transfer tube 3510 may have a proximal end 3511 and a distal end 3512 and a central lumen extending along a longitudinal axis from the proximal end 3511 to the distal end 3512. The central lumen of the distal transfer tube may comprise a minimum diameter configured to receive the distal section 34 and allow the distal section 34 to be readily axially translated (e.g., slid) there through. The central lumen of the proximal transfer tube 3510 may be configured to be placed in fluid communication with the central lumen of the distal transfer tube 3520 when the transfer tubes 3510, 3520 are docked together. The longitudinal axis of the proximal transfer tube 3510 and the distal transfer tube 3520 may be collinear. The distal end 3512 of the proximal transfer tube 3510 may be removably attachable and/or receivable within the proximal end 3521 of the distal transfer tube 3520. The proximal transfer tube 3510 may serve to introduce the distal section 34 of catheter 10 into the proximal end 3521 of the distal transfer tube 3520 such that the distal section 34 may be insertable into the lumen of the proximal section 33. In some embodiments, the proximal transfer tube 3510 and/or the distal transfer tube 3520, or portions thereof, may be entirely or partially transparent. The transparency of one or both of the transfer tubes 3510, 3520 may facilitate the user observing the relative positioning of the catheter 10 or of either of its sections 33, 34 within the vacuum transfer tool 3500.

The proximal transfer tube 3510 may comprise a proximal aspiration port 3513 and the distal transfer tube 3520 may comprise a distal aspiration port 3523. The proximal aspiration port 3513 and/or the distal aspiration port 3523 may be positioned between the proximal and distal ends of their respective transfer tubes 3510, 3520. The aspiration ports 3513, 3523 may be in fluid communication with the central lumens of the transfer tubes 3510, 3520, respectively. The aspiration ports 3513, 3523 may extend outwardly from the central longitudinal axis of the transfer tubes 3510, 3520. The aspiration ports 3513, 3523 may be coupled to one or more vacuum sources for providing vacuum pressure to the catheter 10 via aspiration lines (e.g., plastic tubing). In some implementations, the aspiration ports 3513, 3523 are connected to separate vacuum sources. In some implementations, the aspiration ports 3513, 3523 are connected to a single vacuum source. The single vacuum source may be connected to the aspiration ports 3513, 3523 through a tube splitter. The connection between the single vacuum source and the aspiration ports 3513, 3523 may include one or more valves (e.g., a three-way stopcock) which may selectively regulate the flow to the individual aspiration ports 3513, 3523. For instance, a valve may open fluid communication between both the aspiration ports 3513, 3523 and the vacuum source, between only one of the aspiration ports 3513, 3523 and the vacuum source, or between neither of the aspiration ports 3513, 3523 and the vacuum source. The one or more vacuum sources may be operatively coupled to the aspiration ports 3513, 3523 via removable connections, such as plastic tubing that forms removable fluid-tight seals with the aspiration ports 3513, 3523.

In embodiments in which the distal transfer tube 3520 is removably attachable to the proximal section 33 of catheter 10 or to a separate manifold, the distal end 3522 may comprise connecting means 3524 for connecting to the proximal section 33 or manifold and forming a fluid seal with the proximal section 33 or manifold. For example, the connecting means may comprise a hemostasis valve, such as a rotating hemostasis valve. The proximal end of the proximal section 33 may be received within the connecting means and secured therein, such that the lumen of the proximal section 33 is placed in fluid communication with the central lumen of the distal transfer tube 3520. The proximal end 3521 of the distal transfer tube 3520 may comprise a proximal port 3525 for forming a fluid seal with the distal end 3512 of the proximal transfer tube 3510 and/or the distal section 34 of the catheter 10. The proximal seal 3525 may be configured to removably receive the distal end 3512 of the proximal transfer tube 3510 and/or the distal section 34. In preferred embodiments, the proximal port 3525 may be a self-sealing port configured to automatically form a fluid-tight seal as the distal end 3512 of the proximal transfer tube 3510 and/or distal section 34 is received into and/or withdrawn from the proximal end 3522 of the distal transfer tube 3520. For instance, the self-sealing port may comprise an opening which automatically adjusts in size to the size of the distal end 3512 of the proximal transfer tube 3510 as the proximal transfer tube 3510 is translated axially relative to the port and which forms a fluid seal with the ambient environment when the distal section 34 is subsequently withdrawn, as described elsewhere herein. In some embodiments, the self-sealing port may comprise an elastomeric material which is punctured by the distal end 3512 of the proximal transfer tube 3510 and which effectively reseals upon withdraw of the distal section 33. In some embodiments, the self-sealing port may comprise mechanical means as known in the art for forming automatically forming a fluid seal with a component of variable diameter. In some embodiments, the self-sealing port may be removably attachable to the proximal end 3521 of the distal transfer tube 3520 (e.g., via a rotating hemostasis valve), for example as an adaptor component, and may be replaceable and/or interchangeable. The distal transfer tube 3520 when fluidly sealed to the proximal end of the proximal section 33 of the catheter 10 may be configured to maintain a vacuum around the proximal end of the proximal section 33 via the distal aspiration port 3523 regardless of whether the proximal transfer tube 3510 and/or distal section 34 of catheter 10 are present within, absent from, being inserted into, or being withdrawn from the distal transfer tube 3520.

The distal end 3512 of the proximal transfer tube 3510 may comprise an introducer 3514 for introducing the distal section 34 of catheter 10 into the distal transfer tube 3520. The introducer 3514 may comprise a substantially rigid tubular member configured to be received by the proximal port 3525 of the distal transfer tube 3520. The tubular member may be more rigid than the distal section 34 of the catheter 10, particularly or at least more rigid than the distal end 38 of the distal section 34, which may be highly flexible. The rigid tubular member may facilitate insertion of the distal section 34 of catheter 10 into the proximal port 3525, particularly if the proximal port 3525 is a self-sealing port, as the rigid tubular member may provide better pushability and/or navigability into the port 3525 than the distal end 38 of distal section 34. The introducer 3514 may comprise a stepped-up outer diameter wherein the step is configured to abut the proximal end 3521 of the distal transfer tube 3520 and prevent further insertion of the proximal transfer tube 3510 into the distal transfer tube 3520. Once the introducer 3514 forms a fluid seal with the distal transfer tube 3520, the distal end 14 of distal section 34 can be extended from within and/or inserted through the introducer 3514 into the distal transfer tube 3520. The internal diameter of the rigid tubular member of the introducer 3514 may be at least slightly larger than the largest outer diameter of the distal section 34 of the catheter 10, such that the distal section 34 may be readily translated through the introducer 3514. The central lumen of the distal transfer tube 3520 may be configured to guide the distal section 34 of the catheter 10 into the proximal section 33 of the catheter 10.

In some embodiments, the introducer 3514 may be removably attachable to the distal end 3512 of the proximal transfer tube 3510 (e.g., via a rotating hemostasis valve), for example as an adaptor component, and may be replaceable and/or interchangeable (e.g., to better accommodate various sizes of catheters). While the self-sealing embodiment of the proximal port 3525 may be configured to adjustably seal the distal transfer tube 3520 relative to components of variable size, in some embodiments, the dimensions of the introducer 3514 and the proximal port 3525 of the distal transfer tube 3520 may be optimally configured to form a fluid seal with one another. For example, the self-sealing opening may be configured to form an especially tight fluid seal with a component having the outer diameter of the introducer 3514. The outer diameter of the introducer 3514 may correspond to the maximum diameter of the self-sealing port 3525, under which maximum pressure may be exerted against the introducer 3514 by the seal. The introducer 3514 may provide a static interface between the proximal transfer tube 3510 and the distal transfer tube 3520 that allows ready translation of the distal section 34 within the vacuum transfer tool 3500 without compromising the fluid seal between the two transfer tubes 3510, 3520.

In some embodiments, the vacuum transfer tool 3500 may comprise a locking mechanism or securing mechanism (not shown) configured to releasably secure the proximal transfer tube 3510 (e.g., introducer 3514) to the distal transfer tube 3520 (e.g., proximal port 3525) to prevent the two from becoming inadvertently separated during use. The locking mechanism may comprise components coupled to the proximal transfer tube 3510 and/or the distal transfer tube and may comprise one or more components such as latches, clasps, clamps, threaded connectors, easily removable pins, etc. The locking mechanism may be easily engaged after the distal end 3512 of the proximal transfer tube 3510 is inserted into the proximal end 3521 of the distal transfer tube 3520 and easily disengaged prior to removing the distal end 3512 of the proximal transfer tube 3510 from the proximal end 3521 of the distal transfer tube 3520. In some embodiments, the proximal transfer tube 3510 and distal transfer tube 3520 may be sufficiently secured without an additional locking mechanism. For example, in some embodiments, the length of the introducer 3514 may be a length sufficient to steadily dock and maintain the distal end 3512 of the proximal transfer tube 3510 within the distal transfer tube 3520 even with inadvertent movement of the two transfer tubes 3510, 3520.

The proximal end 3511 of the proximal transfer tube 3510 may comprise a proximal sealing port 3515. The proximal sealing port 3515 may be configured to removably receive the distal section 34 of the catheter 10. The proximal sealing port 3515 may be configured to form a fluid seal around the distal section of catheter 10. In some embodiments, the proximal sealing port 3515 may be a hemostasis valve, such as a rotating hemostasis valve. The rotating hemostasis valve may comprise an openable/closeable seal and a rotatable collar that controls the opening and closing of a seal, as is known in the art. Rotating the collar in one direction may open the seal while rotating the color in the opposite direction may close the seal. The size of the opening formed by the seal may be adjustable by the rotatable collar. The seal may be closed around the pull wire 42 to an extent that substantially seals the inside of the proximal transfer tube 3510, around the pull wire 42, from the ambient environment, but which allows axial translation of the distal section 34 without breaking the fluid seal. In some embodiments, the proximal sealing port 3515 may be a self-sealing port, as described elsewhere herein.

The proximal transfer tube 3510 may comprise two openable/closeable fluid seals 3516, 3517 surrounding the proximal aspiration port 3513. A first fluid seal 3516 may be positioned on a proximal side of the proximal aspiration port 3513 and a second fluid seal 3517 may be positioned on a distal side of the proximal aspiration port 3513. The first fluid seal 3516 and/or the second fluid seal 3517 may be hemostasis valves, such as rotating hemostasis valves. In some embodiments, as shown in FIGS. 14A and 14C, the first fluid seal 3516 may be the proximal sealing port 3515 of the proximal transfer tube 3510. In other embodiments, the first fluid seal 3517 may be a separate seal positioned between the proximal sealing port 3515 and the proximal aspiration port 3513. The first and second fluid seals 3516, 3517 may be configured to form an airtight environment within the central lumen of the proximal transfer tube 3510 between the seals 3516, 3517 which is in fluid communication with the proximal aspiration port 3513. The first and second fluid seals 3516, 3517 may be used to trap a vacuum formed by the proximal aspiration port 3513 around the proximal end 36 of the distal section 34 of catheter 10, as described elsewhere herein. In some implementations, manually adjustable seals, such as rotating hemostasis valves, may form better fluid seals than self-sealing seals, particularly with respect to larger diameter components, while self-sealing seals may allow for easier translation of a component through the seal without breaking the seal.

FIGS. 15A-15D schematically illustrate example configurations of the vacuum transfer tool 3500 during the illustrative, but non-limiting, example of use with the catheter 10 described hereafter. The various components may not be drawn to scale. The vacuum transfer tool 3500 may be used to introduce and remove the distal section 34 of catheter 10 into the proximal section 33 of the catheter 10. The proximal transfer tube 3510 may be configured to maintain a vacuum on the proximal end 36 of distal section 34, even as the proximal end 36 is proximally retracted beyond the proximal end 3521 of the distal transfer tube 3520. Thus, the lumen 40 of the distal section 34 will not provide a fluid pathway between the distal transfer tube 3520 and the ambient atmosphere, effectively preventing or inhibiting loss of vacuum pressure at the distal end of the proximal section 33 of the catheter 10. Also, vacuum pressure will be maintained on both the distal end of the proximal section 33 and the distal end 38 of the distal section 34, after the distal end 38 is removed from the distal transfer tube 3520.

Figure 15A:
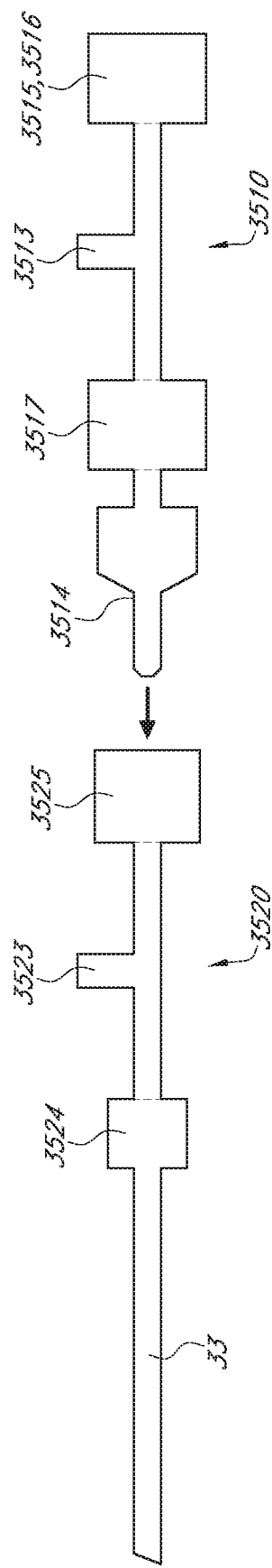
FIGS. 15A-15D schematically illustrate cross sections of the vacuum transfer device during an example of a procedure for capturing a clot on a distal end of the proximal section of the catheter and maintaining vacuum on the proximal section during removal of the extendable distal section of the catheter from the proximal section.

As shown in FIG. 15A, in one embodiment, the distal transfer tube 3520 may be coupled to the proximal section 33 of catheter 10 (or to a manifold connected to proximal section 33) and the proximal transfer tube 3510 may then be coupled to or docked with the distal transfer tube 3510 by inserting the introducer 3514 into and through the proximal port 3525 of the distal transfer tube 3520. The proximal transfer tube 3510 and distal transfer tube 3520 may be locked together in embodiments comprising a locking mechanism. Alternatively, the two transfer tubes 3510, 3520 could be coupled prior to connecting the distal transfer tube 3520 to the proximal section 33 of catheter 10, if the distal transfer tube 3520 is a separable component from the proximal section 33. Prior to initiating the aspiration procedure, either or both of the aspiration ports 3513, 3523 may be connected to an irrigation source (e.g., a saline solution) to allow flushing through the catheter 10. In some embodiments, one of the ports may be connected to the irrigation source and the other to a vacuum source. In some embodiments, both aspiration ports 3513, 3523 may be connected to a vacuum source.

Figure 15B:
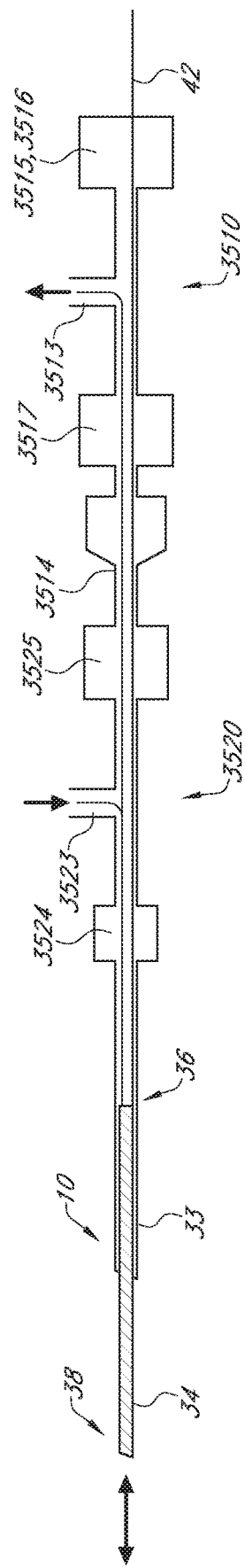

As shown in FIG. 15B, the distal section 34 of catheter 10 can be introduced into the vacuum transfer tool 3500 via the proximal sealing port 3515 of the proximal transfer tube 3510. The distal section 34 may be advanced through the introducer 3514 into the central lumen of the distal transfer tube 3520 and within the central lumen of the distal transfer tube 3520 into the lumen of the proximal section 33. The distal section 34 may be selectively extended within the proximal section 33 such that the distal end 38 of the distal section 34 may be extended beyond the distal section of the proximal section and/or retracted relative to the proximal section 33 as desired. The second seal 3517 may be maintained in an open position during the introduction of section 34 of the catheter 10. The first seal 3515 may be maintained in an open position during the introduction if it is separate from the proximal sealing port 3515. The proximal sealing port 3515 may be opened, at least partially, to allow the introduction of the distal section 34 of catheter 10 into the vacuum transfer tool 3500. Once the proximal end 36 of the distal section 34 is positioned within the vacuum transfer tool 3500, the proximal sealing port 3515 may be closed, at least partially, around the pull wire 42, which may extend from the proximal end of the vacuum transfer tool 3500 to allow the user to extend and retract the distal section 34 of the catheter 10 relative to the proximal section 33. The proximal sealing port 3515 may be closed as much as possible to optimally seal the vacuum transfer tool 3500 while not preventing or unduly interfering with the axial translation of the pull wire 42 (e.g., via excess friction). The rigid construction of the pull wire 42 (e.g., a metal rod or hypotube) may allow the pull wire 42 to slide relatively easily through a tight fluid seal of the proximal sealing port 3515 (e.g., be relatively pushable) without collapsing any internal lumen, particularly as compared to the more flexible catheter 10. In some implementations, vacuum is not applied to the catheter 10 until the proximal end 36 of the distal section 34 is positioned within the vacuum transfer tool 3500 and the proximal sealing port 3515 is closed around the pull wire 42. In some implementations, vacuum is not applied to catheter 10 until the distal section 34 is fully extended, or at least extended as far as it will be extended during the aspiration procedure. Once the distal section 34 is fully or optimally extended, the proximal sealing port 3515 may be closed even tighter around the pull wire 42, in some implementations, for the aspiration procedure. In some implementations, irrigation may remain connected to one of the aspiration ports 3513, 3523. Irrigation fluid may be sucked into the other aspiration port through which vacuum is applied when the vacuum is on, but may be flushed through the catheter 10 when the vacuum is off (e.g., during a pulsing sequence). In some implementations, vacuum may be applied to both aspiration ports 3513, 3523.

Figure 15C:
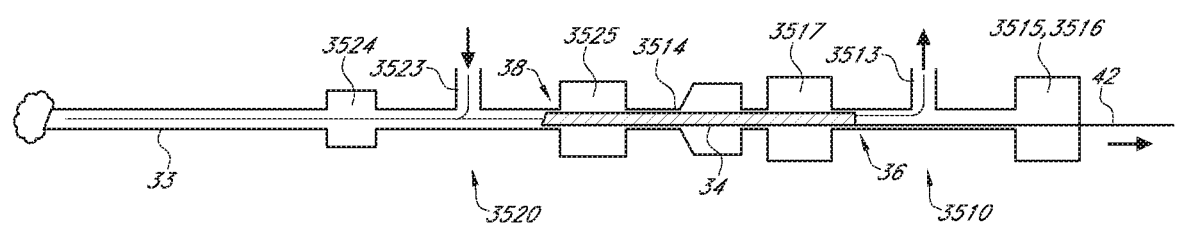

FIG. 15C illustrates a clot corked on the distal end of the proximal section 33 of the catheter 10 after the distal end 38 of the distal section 34 has been retracted to a position within the proximal section 33 or the proximal transfer tube 3520. Prior to retracting the distal section 34, the proximal sealing port 3515 may be slightly opened to allow easier movement of the pull wire 42 through the proximal sealing port 3515 without losing vacuum pressure. As described elsewhere herein, the distal section 34 may be removed from proximal section 33 and distal transfer tube 3520 to increase the effective cross-sectional area within the proximal section 33. Prior to removing the distal section 34 vacuum may be applied to both the proximal aspiration port 3513 and the distal aspiration port 3523. The vacuum may be applied to both aspiration ports 3513, 3523 prior to capturing the clot. The distal section 34 may be proximally withdrawn until the proximal end 36 of the distal section 34 is positioned within the proximal transfer tube 3510 between the first seal 3516 and the second seal 3517. The position of the proximal end 36 may be visually ascertained through the proximal transfer tube 3510 and/or another suitable indicator may be used, such as a marking on the pull wire 42 which may be configured to become visible (i.e. emerge from the proximal sealing port 3515) when the proximal end 36 of distal section 34 is in the proper position. At this point, first and second seals 3516, 3517 may be fully closed. The first seal 3516 may be closed around the pull wire 42. The second seal 3517 may be closed around a proximal portion of the distal section 34 of catheter 10. The closure of the fluid seals 3516, 3517 may firmly secure the proximal transfer tube 3510 to the distal section 34 of the catheter 10 such that the two components are readily movable as a single unit. The tight closing of the first and second seals 3516, 3517 around the proximal end 36 of the distal section 34 may optimize the fluid seal around the proximal end 36 of the distal section 34 since the distal section 34 no longer need be axially translated with respect to the proximal transfer tube 3510. In some implementations, the vacuum may be disconnected or rerouted from the proximal aspiration port 3513 after the seals 3516, 3517 are closed as long as the existing vacuum pressure within the proximal transfer tube 3510 is not released through the proximal aspiration port 3513.

Figure 15D:
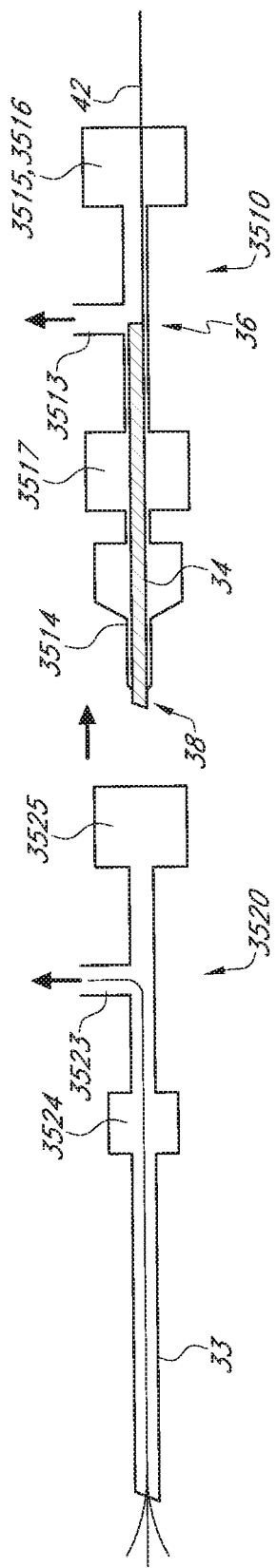

FIG. 15D illustrates the undocking or decoupling of the proximal transfer tube 3510 from the distal transfer tube 3520. Once the first and second seals 3516, 3517 are closed forming a fluid seal around the proximal end 36 of distal section 34 of catheter 10, the proximal transfer tube 3510 and the distal transfer tube 3520 may be separated by proximally withdrawing the proximal transfer tube 3510, which simultaneously withdrawals the distal section 34 firmly secured to the proximal transfer tube 3510. Once the introducer 3514 is withdrawn from the distal transfer tube 3520, a fluid seal may be performed between the distal section 34 of the catheter 10 and the proximal sealing port 3525 of the distal transfer tube 3520. The proximal sealing port 3525, if a self-sealing port, may automatically form a seal with the distal section 34, which has a smaller outer diameter than the introducer 3514, and may automatically adjust to any changes in the outer diameter of the distal section 34 as it is withdrawn, such as a taper at the distal end 38 of the distal section 34. The fluid seal formed by closing the second seal 3517 of the proximal transfer tube 3510 around the distal section 34 prevents vacuum pressure being lost through the gap between the introducer 3514 and the distal section 34, once the introducer 3514 is separated from the distal transfer tube 3520 and the gap is no longer in fluid communication with the distal aspiration port 3523. The vacuum trap formed around the proximal end 36 of the distal section 34 by the proximal transfer tube 3510 may advantageously prevent any clot that is stuck on the end of the distal section 34 from being lost as the distal section 34 is withdrawn. During and after withdraw of the distal section 34, vacuum pressure is continually maintained on the proximal section 33 of the catheter via the distal aspiration port 3523.

In some embodiments, additional instrumentation may be inserted into the proximal section 33 of the catheter 10 through the proximal port 3525 of the distal transfer tube 3520 before coupling of the proximal transfer tube 3510 or after decoupling of the proximal transfer tube 3510. For instance, an agitator device may be inserted into the lumen of the proximal section 33 to help unclog any clots from the lumen. The agitator may take advantage of an increased lumen size once the distal section 34 is removed to more effectively release a clot from the distal end or lumen of the proximal section 33, allowing the clot to be aspirated via aspiration port 3523. In some embodiments, additional instrumentation may be inserted into the distal section 34 of the catheter 10 through the proximal seal 3515. The proximal seal 3515 may be closed around the additional instrumentation similar to the control wire 42. In some embodiments, the additional instrumentation may be inserted into the proximal transfer tube 3510 via a separate manifold (e.g., another transfer tube) that is configured to couple with the proximal end 3511 (e.g., proximal seal 3515) of the proximal transfer tube 3510. The additional manifold or transfer tube may comprise its own aspiration port for maintaining vacuum pressure. In some embodiments, the pull wire 42 may be a hypotube comprising an internal central lumen 45, as described elsewhere herein. The central lumen 45 may be maintained under vacuum or under positive pressure (e.g., an irrigation fluid) such that it does not provide a pressure release to the transfer tool 3500 or the lumen may be sized such that the any pressure release is insignificant. In some embodiments, additional instrumentation, such as an agitotator, may be inserted into the catheter 10 via the central lumen 45. In some implementations, the additional instrumentation may be coupled to a proximal end of the pull wire 42 via a separate manifold. The manifold may be decoupled from the transfer tube 3500 or it may be configured to couple to the proximal end 3511 (e.g., proximal seal 3515) of the proximal transfer tube 3510.

Any of the catheter shaft or sections of the catheter shaft or telescoping extensions in accordance with the present invention, such as inner device 3402 or outer device 3404, may comprise a multi-layer construct having a high degree of flexibility and sufficient push ability to reach deep into the cerebral vasculature, such as at least as deep as the petrous, cavernous, or cerebral segment of the internal carotid artery (ICA).

Figure 16:
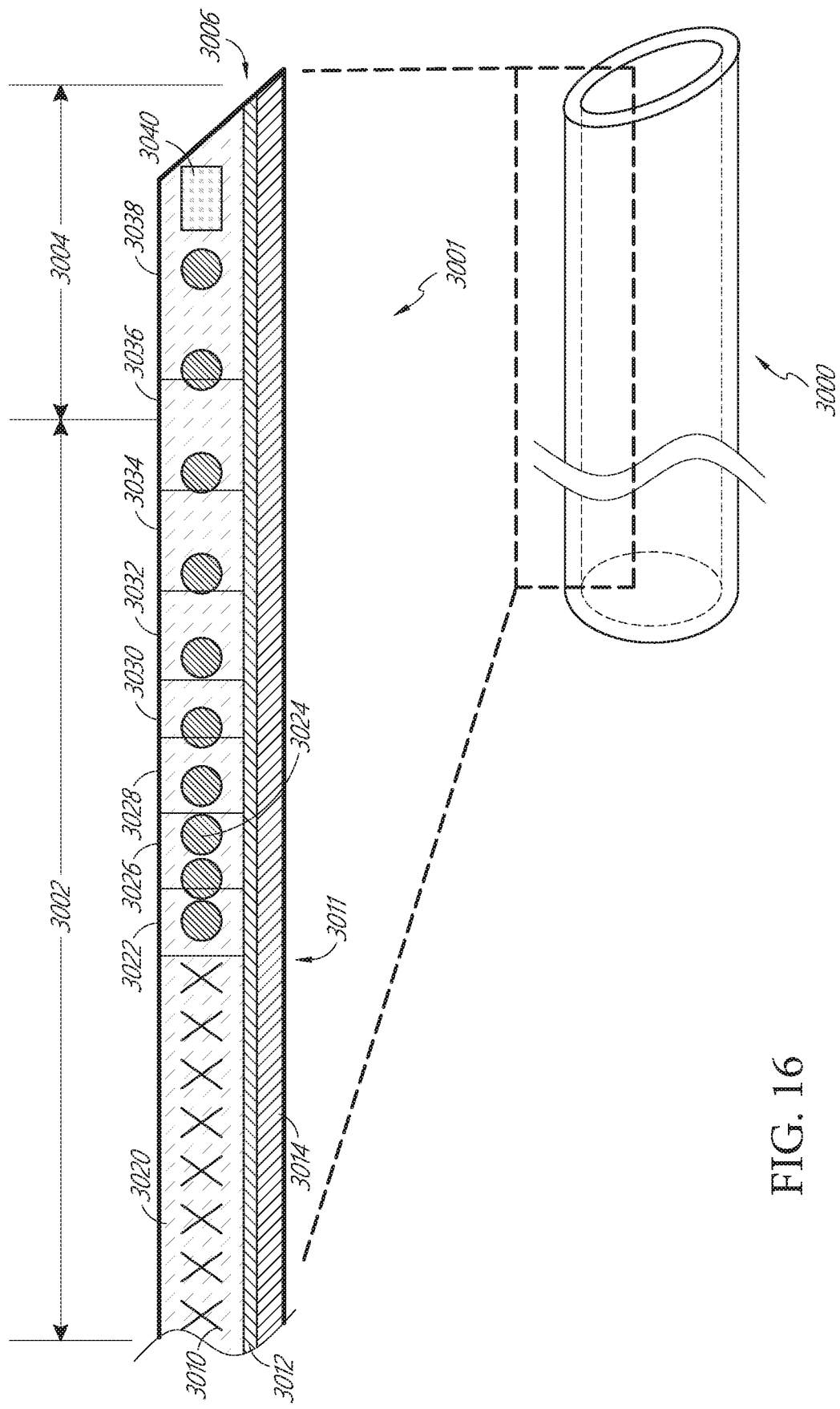
FIG. 16 illustrates a cross-sectional elevational view of a catheter wall according to an embodiment.

In one example, referring to FIG. 16, a catheter 3000, which may be the same or similar to device 3400, may have an effective length from the manifold to distal tip from about 70 cm to about 150 cm, from about 80 cm to about 140 cm, from about 90 cm to about 130 cm, from about 100 cm to about 120 cm, or from about 105 cm to about 115 cm. The outer diameter of the catheter 3000 may be from about 0.07 inches to about 0.15 inches, from about 0.08 inches to about 0.14 inches, from about 0.09 inches to about 0.13 inches, from about 0.1 inches to about 0.12 inches, or from about 0.105 inches to about 0.115 inches, and may be lower in a distal segment than in a proximal segment. The inner diameter 3108 of the catheter 3000 in a single central lumen embodiment may be greater than or equal to about 0.11 inches, greater than or equal to about 0.1 inches, greater than or equal to about 0.09 inches, greater than or equal to about 0.088 inches, greater than or equal to about 0.08 inches, greater than or equal to about 0.07 inches, greater than or equal to about 0.06 inches, or greater than or equal to about 0.05 inches. The inner diameter 3108 of the catheter 3000 in a single central lumen embodiment may be less than or equal to about 0.11 inches, less than or equal to about 0.1 inches, less than or equal to about 0.09 inches, less than or equal to about 0.088 inches, less than or equal to about 0.08 inches, less than or equal to about 0.07 inches, less than or equal to about 0.06 inches, or less than or equal to about 0.05 inches. Referring to FIG. 16, an inner liner 3014 may be formed by dip coating a mandrel (not shown) to provide a thin walled tubular inside layer of the catheter body 3000. The dip coating may be produced by coating a wire such as a silver coated copper wire in PTFE. The mandrel may thereafter be axially elongated to reduce diameter, and removed to leave the tubular inner liner. The outside surface of the tubular inner liner 3014 may thereafter be coated with a soft tie layer 3012 such as polyurethane (e.g., Tecoflex™), to produce a layer having a thickness of no more than about 0.005 inches, and in some implementations approximately 0.001 inches. The tie layer 3012 will generally extend along at least about the most distal 10 cm or 20 cm of the catheter shaft 3000 generally less than about 50 cm and may in one implementation extend approximately the distal 30 cm of catheter shaft 3000, 3100.

A braid such as a 75 ppi stainless steel braid 3010 may thereafter be wrapped around the inner liner 3014 through a proximal zone up to a distal transition 3011. From the distal transition 3011 to the distal end of the catheter 3000, a coil 3024 comprising a shape memory material such as a Nitinol alloy may thereafter be wrapped around the inner liner 3014. In one implementation, the Nitinol coil has a transition temperature below body temperature so that the Nitinol resides in the austinite (springy) state at body temperature. Adjacent loops or filars of the coil 3024 may be closely tightly wound in a proximal zone with a distal section having looser spacing between adjacent loops. In an embodiment having a coil section 3024 with an axial length of at least between about 20% and 30% of the overall catheter length, (e.g., 28 cm coil length in a 110 cm catheter shaft 3000), at least the distal 1 or 2 or 3 or 4 cm of the coil will have a spacing that is at least about 130%, and in some implementations at least about 150% or more than the spacing in the proximal coil section. In a 110 cm catheter shaft 3000 having a Nitinol coil the spacing in the proximal coil may be about 0.004 inches and in the distal section may be at least about 0.006 inches or 0.007 inches or more. In embodiments comprising an extension catheter, the distal extendable section of the catheter may be constructed according to the foregoing. The length of the coil 3024 may be proportioned to the length of the extendable catheter segment or the total (e.g., extended) length of the catheter 3000. The coil 3024 may extend from a distal end of the extendable segment over at least about 50%, 60%, 70%, 80%, or 90% of the length of the extendable segment. In some embodiments, the catheter 3000 or the extendable segment may not comprise a braid and the coil 3024 may extend to the proximal end of the extendable segment (100% of the length).

The distal end of the coil 3024 can be spaced proximally from the distal end of the inner liner 3014, for example, to provide room for an annular radiopaque marker 3040. The coil 3024 may be set back proximally from the distal end, in some embodiments, by approximately no more than 1 cm, 2 cm, or 3 cm. In one embodiment, the distal end of the catheter 3000 is provided with a beveled distal surface 3006 residing on a plane having an angle of at least about 10° or 20° and in one embodiment about 30° with respect to a longitudinal axis of the catheter 3000. The radiopaque marker 3040 may reside in a plane that is transverse to the longitudinal axis. Alternatively, at least the distally facing edge of the annular radiopaque marker 3040 may be an ellipse, residing on a plane which is inclined with respect to the longitudinal axis to complement the bevel angle of the distal surface 3006.

After applying the proximal braid 3010, the distal coil 3024 and the RO marker 3040 an outer Jacket 3020 maybe applied such as a shrink wrap tube to enclose the catheter body 3000. The outer shrink-wrapped sleeve 3020 may comprise any of a variety of materials, such as polyethylene, polyurethane, polyether block amide (e.g., PEBAX™), nylon or others known in the art. Sufficient heat is applied to cause the polymer to flow into and embed the proximal braid and distal coil.

In one implementation, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 3000 and provide a smooth continuous outer tubular body. The foregoing construction may extend along at least the most distal 10 cm, and preferably at least about the most distal 20 cm, 25 cm, 30 cm, 35 cm, 40 cm, or more than 40 cm of the catheter body 3000. The entire length of the outer shrink wrap jacket 3020 may be formed from tubular segments and the length of the distal tubular segments (e.g., 3022, 3026, 3028, 3030, 3032, 3034, 3036, 3038) may be shorter than the one or more tubular segments forming the proximal portion of the outer shrink wrap jacket 3020 in order to provide steeper transitions in flexibility toward the distal end of the catheter 3000.

The durometer of the outer wall segments may decrease in a distal direction. For example, proximal segments such as 3022 and 3026, may have a durometer of at least about 60 or 70 D, with gradual decrease in durometer of successive segments in a distal direction to a durometer of no more than about 35 D or 25 D or lower. A 25 cm section may have at least about 3 or 5 or 7 or more segments and the catheter 3000 overall may have at least about 6 or 8 or 10 or more distinct flexibility zones. The distal 1 or 2 or 4 or more segments 3036, 3038, may have a smaller OD following shrinking than the more proximal segments 3022-3034 to produce a step down in OD for the finished catheter body 3000. The length of the lower OD section 3004 may be within the range of from about 3 cm to about 15 cm and in some embodiments is within the range of from about 5 cm to about 10 cm such as about 7 or 8 cm, and may be accomplished by providing the distal segments 3036, 3038 with a lower wall thickness.

Figure 17A:
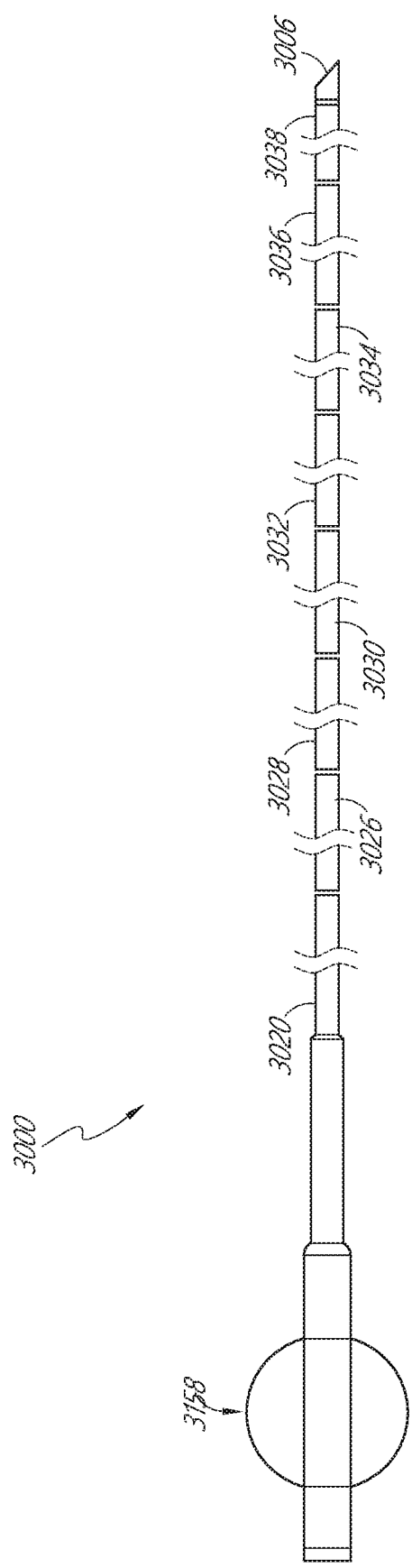
FIG. 17A illustrates a side elevational view of a progressively enhanced flexibility catheter according to an embodiment.
Figure 17B:
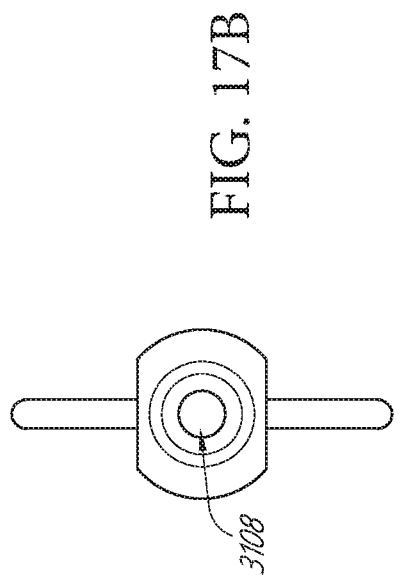
FIG. 17B is a proximal end view of the enhanced flexibility catheter of FIG. 17A.

Referring to FIGS. 17A-17B, there is illustrated one example of an outer jacket segment stacking pattern for a progressive flexibility catheter of the type discussed in connection with FIG. 15. A distal segment 3038 may have a length within the range of about 1-3 cm, and a durometer of less than about 35D or 30D. An adjacent proximal segment 3036 may have a length within the range of about 4-6 cm, and a durometer of less than about 35D or 30D. An adjacent proximal segment 3034 may have a length within the range of about 4-6 cm, and a durometer of about 35D or less. An adjacent proximal segment 3032 may have a length within the range of about 1-3 cm, and a durometer within the range of from about 35D to about 45D (e.g., 40D). An adjacent proximal segment 3030 may have a length within the range of about 1-3 cm, and a durometer within the range of from about 50D to about 60D (e.g., about 55D). An adjacent proximal segment 3028 may have a length within the range of about 1-3 cm, and a durometer within the range of from about 35D to about 50D to about 60D (e.g., about 55D). An adjacent proximal segment 3026 may have a length within the range of about 1-3 cm, and a durometer of at least about 60D and typically less than about 75D. More proximal segments may have a durometer of at least about 65D or 70D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10D, preferably at least about 20D and in some implementations at least about 30D or 40D or more.

In another embodiment, the most distal portion of the catheter 3000 may comprise a durometer of less than approximately 35D (e.g., 25D) to form a highly flexible distal portion of the catheter and have a length between approximately 25 cm and approximately 35 cm. In other embodiments, the length may be between approximately 15 cm and approximately 25 cm. The distal portion may comprise one or more tubular segments of the same durometer (e.g., segment 3038) or of different durometers. In some embodiments, one or more of the distal most segments may comprise a polyether-based thermoplastic polyurethane (e.g., Tecothane®). More proximal segments may comprise a polyether block amide (e.g., PEBAX®). A series of proximally adjacent tubular segments to the distal portion may form a transition region between a proximal stiffer portion of the catheter 3000 and the distal highly flexible portion of the catheter. The series of tubular segments forming the transition region may have the same or substantially similar lengths, such as approximately 1 cm. The relatively short length of the series of tubular segments may provide a steep drop in durometer over the transition region. For example, the transition region may have a proximal tubular segment 3036 (proximally adjacent the distal portion) having a durometer of approximately 35D. An adjacent proximal segment 3034 may have a durometer of approximately 55D. An adjacent proximal segment 3032 may have a durometer of approximately 63D. An adjacent proximal segment 3030 may have a durometer of approximately 72D. One or more of the segments within the transition region may comprise a length between about 1 and 4 cm. For example, the transition region may comprise a proximal segment 3036 approximately 4 cm and 35D, an adjacent segment 3034 approximately 3 cm and 37D, an adjacent segment 3032 approximately 1 cm and 47D, an adjacent segment 3030 approximately 1 cm and 55D, an adjacent segment 3028 approximately 1 cm and 63D, and an adjacent segment 3026 approximately 1 cm and 72D. In some embodiments, the length of the distal portion of the catheter 3000, including the highly flexible distal portion and the transition region, may be between about 25-30 cm, between about 30-35 cm, between about 35 to 40 cm, or between about 40-45 cm. More proximal segments may comprise a durometer or durometers greater than approximately 72D and may extend to the proximal end of the catheter or extension catheter segment. For instance, an extension catheter segment may comprise a proximal portion greater than approximately 72D between about 1 cm and about 3 cm. In some embodiments, the proximal portion may be about 2 cm long. In some embodiments, the most distal segments (e.g., 3038-3030) or at least the transition region may comprise PEBAX® and more proximal segments may comprise a generally stiffer material, such as Vestamid®.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vacuum transfer tool for maintaining a vacuum within an extendable catheter, the vacuum transfer tool comprising:
    a proximal transfer tube comprising:
        a proximal end comprising a proximal sealing port being configured to receive and form a fluid seal around an extendable catheter segment,
        a distal end,
        a lumen extending from the proximal end to the distal end, and
        an aspiration port in fluid communication with the lumen, the aspiration port being positioned between the proximal end and the distal end,
        wherein the proximal transfer tube is configured to form a sealed space between the proximal end and the distal end around the extendable catheter segment;
    a distal transfer tube being configured to receive the extendable catheter segment from the proximal transfer tube and to position the extendable catheter segment within a lumen of a catheter, the distal transfer tube comprising:
        a proximal end being removably connectable to the distal end of the proximal transfer tube,
        a distal end being directly or indirectly connectable to a proximal end of the catheter,
        a lumen extending from the proximal end to the distal end, and
        an aspiration port in fluid communication with the lumen and being configured to engage an aspiration source to provide vacuum pressure to the catheter, the aspiration port being positioned between the proximal end and the distal end, the aspiration port comprising a valve configured to regulate fluid flow through the aspiration port.

2. The vacuum transfer tool of claim 1, wherein the proximal end of the distal transfer tube comprises a fluid sealing port.

3. The vacuum transfer tool of claim 2, wherein the fluid sealing port is a self-sealing port.

4. The vacuum transfer tool of claim 1, wherein the distal transfer tube is removably connectable directly or indirectly to the proximal end of the catheter.

5. The vacuum transfer tool of claim 1, wherein the distal end of the proximal transfer tube comprises an introducer configured to be received within the lumen of the distal transfer tube.

6. The vacuum transfer tool of claim 5, wherein the introducer comprises a rigid tubular body.

7. The vacuum transfer tool of claim 6, wherein the introducer comprises a step adjacent the rigid tubular body, the step configured to abut the proximal end of the distal transfer tube.

8. The vacuum transfer tool of claim 5, wherein the proximal transfer tube comprises a rotating hemostasis valve between the introducer and the aspiration port configured to help form the sealed space.

9. The vacuum transfer tool of claim 1, wherein the proximal sealing port of the proximal transfer tube is a rotating hemostasis valve.

10. The vacuum transfer tool of claim 1, wherein the proximal transfer tube comprises two rotating hemostasis valves positioned on opposite sides of the aspiration port, the rotating hemostasis valves configured to form the sealed space when closed and configured to secure the extendable catheter segment to the proximal transfer tube when closed such that movement of the proximal transfer tube simultaneously moves the extendable catheter segment.

11. The vacuum transfer tool of claim 1, wherein at least portions of the proximal transfer tube and/or the distal transfer tube are transparent.

12. The vacuum transfer tool of claim 11, wherein the proximal transfer tube is configured to allow visual determination of a positioning of a proximal end of the extendable catheter segment within a portion of the lumen of the proximal transfer tube corresponding to the sealed space.

13. The vacuum transfer tool of claim 1, further comprising the catheter.

14. The vacuum transfer tool of claim 13 further comprising the extendable catheter segment.

* * * * *